United States Patent
Cao et al.

(10) Patent No.: US 11,224,388 B2
(45) Date of Patent: Jan. 18, 2022

(54) IMAGE SENSORS HAVING X-RAY DETECTORS

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 22 days.

(21) Appl. No.: 16/177,709

(22) Filed: Nov. 1, 2018

(65) Prior Publication Data
US 2019/0069858 A1 Mar. 7, 2019

Related U.S. Application Data

(63) Continuation of application No. PCT/CN2016/110937, filed on Dec. 20, 2016.

(51) Int. Cl.
*A61B 6/00* (2006.01)
*G01T 1/24* (2006.01)

(52) U.S. Cl.
CPC .......... *A61B 6/4233* (2013.01); *A61B 6/4452* (2013.01); *A61B 6/5241* (2013.01); *A61B 6/54* (2013.01); *G01T 1/24* (2013.01); *G01T 1/249* (2013.01)

(58) Field of Classification Search
CPC ..... A61B 6/037; A61B 6/0407; A61B 6/4266; A61B 6/4275; A61B 6/5205; A61B 6/4291; A61B 6/4417
See application file for complete search history.

(56) References Cited

U.S. PATENT DOCUMENTS

| | | | |
|---|---|---|---|
| 4,315,157 A * | 2/1982 | Barnes | A61B 6/032 378/10 |
| 4,394,676 A * | 7/1983 | Agouridis | H01L 31/115 257/429 |
| 5,864,146 A * | 1/1999 | Karellas | A61B 6/06 250/581 |
| 6,175,609 B1 | 1/2001 | Edic et al. | |
| 6,236,051 B1 * | 5/2001 | Yamakawa | G01T 1/2928 250/370.01 |
| 7,045,787 B1 | 5/2006 | Verbinski et al. | |
| 7,835,877 B2 * | 11/2010 | Zaman | G06F 1/3203 320/155 |
| 2003/0095631 A1 * | 5/2003 | Rosner | G01N 23/02 378/98.12 |

(Continued)

FOREIGN PATENT DOCUMENTS

| | | |
|---|---|---|
| WO | 2016135106 A1 | 9/2016 |
| WO | 2016161542 A1 | 10/2016 |

*Primary Examiner* — David P Porta
*Assistant Examiner* — Mamadou Faye
(74) *Attorney, Agent, or Firm* — IPRO, PLLC; Qian Gu

(57) ABSTRACT

Disclosed herein is an image sensor comprising: a plurality of X-ray detectors; an actuator configured to move the plurality of X-ray detectors to a plurality of positions, wherein the image sensor is configured to capture, by using the detectors, images of portions of a scene at the positions, respectively, and configured to form an image of the scene by stitching the images of the portions.

30 Claims, 25 Drawing Sheets

(56) References Cited

U.S. PATENT DOCUMENTS

| | | | |
|---|---|---|---|
| 2004/0190676 A1* | 9/2004 | Kojima | G01N 23/046 378/19 |
| 2005/0084073 A1* | 4/2005 | Seppi | A61B 6/032 378/156 |
| 2005/0117696 A1* | 6/2005 | Suzuki | A61B 6/04 378/19 |
| 2006/0076498 A1 | 4/2006 | Hilderscheid et al. | |
| 2007/0280409 A1* | 12/2007 | Konno | A61B 6/032 378/19 |
| 2008/0152088 A1 | 6/2008 | Wang et al. | |
| 2009/0046913 A1* | 2/2009 | Chandra | A61B 6/035 382/131 |
| 2010/0020924 A1* | 1/2010 | Booker | G01T 1/17 378/19 |
| 2011/0038454 A1* | 2/2011 | Minnigh | A61B 6/587 378/62 |
| 2011/0064193 A1* | 3/2011 | Minnigh | A61B 6/505 378/62 |
| 2011/0121191 A1 | 5/2011 | Kappler et al. | |
| 2012/0307967 A1* | 12/2012 | Smith | G01V 5/0016 378/57 |
| 2014/0064446 A1* | 3/2014 | Wear | G01T 1/2018 378/62 |
| 2014/0334600 A1* | 11/2014 | Lee | G01N 23/04 378/62 |
| 2015/0119704 A1* | 4/2015 | Roth | G01T 1/1603 600/425 |
| 2016/0099282 A1* | 4/2016 | Vora | H01L 27/14663 257/428 |
| 2016/0310098 A1* | 10/2016 | Kim | A61B 6/544 |
| 2017/0350990 A1* | 12/2017 | Chmeissani Raad | G01T 1/366 |

* cited by examiner

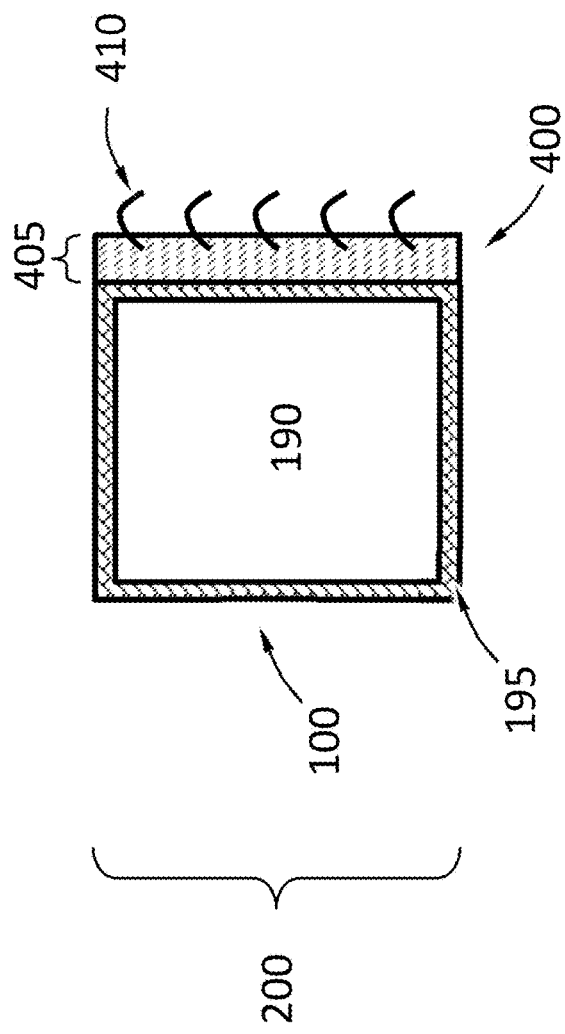
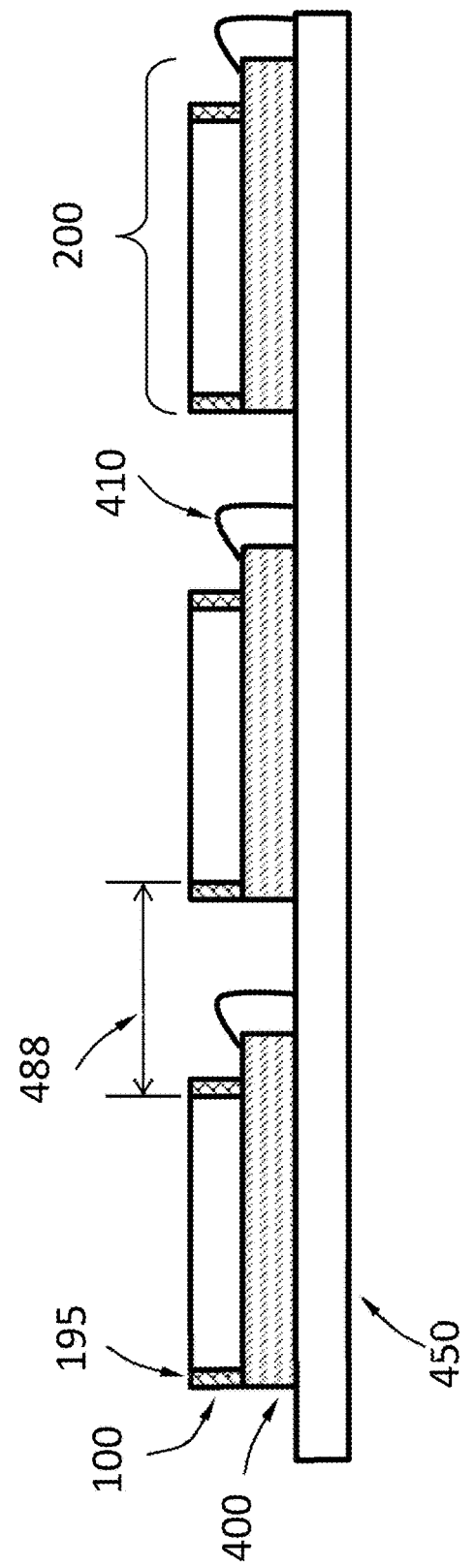

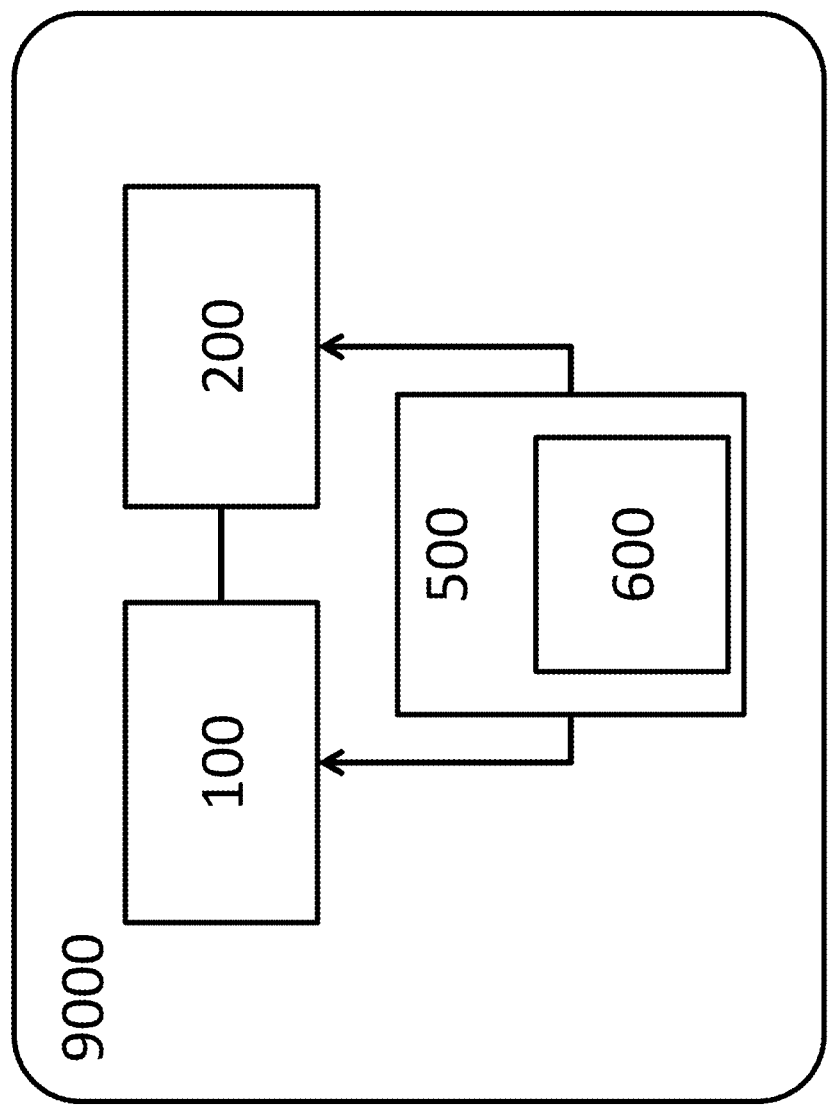

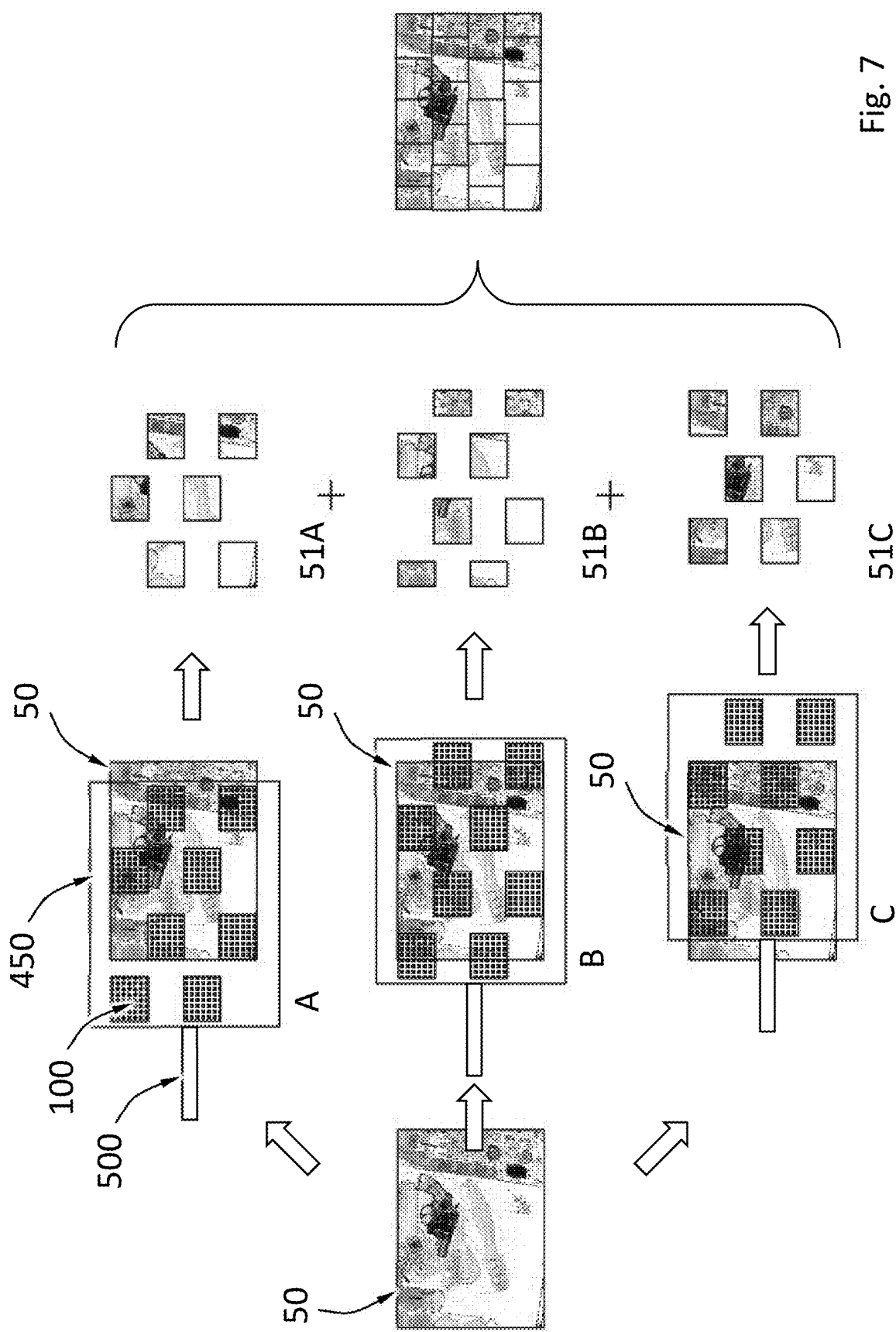

IMAGE SENSORS HAVING X-RAY DETECTORS

TECHNICAL FIELD

The disclosure herein relates to X-ray detectors, particularly relates to image sensors with X-ray detectors and its methods of use.

BACKGROUND

X-ray detectors may be devices used to measure the flux, spatial distribution, spectrum or other properties of X-rays.

X-ray detectors may be used for many applications. One important application is imaging. X-ray imaging is a radiography technique and can be used to reveal the internal structure of a non-uniformly composed and opaque object such as the human body.

Early X-ray detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to X-ray, electrons excited by X-ray are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of X-ray detectors are X-ray image intensifiers. Components of an X-ray image intensifier are usually sealed in a vacuum. In contrast to photographic plates, photographic films, and PSP plates, X-ray image intensifiers may produce real-time images, i.e., do not require post-exposure processing to produce images. X-ray first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident X-ray. The emitted electrons are projected, through electron optics, onto an output phosphor and cause the output phosphor to produce a visible-light image.

Scintillators operate somewhat similarly to X-ray image intensifiers in that scintillators (e.g., sodium iodide) absorb X-ray and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of X-ray. A scintillator thus has to strike a compromise between absorption efficiency and resolution.

Semiconductor X-ray detectors largely overcome this problem by direct conversion of X-ray into electric signals. A semiconductor X-ray detector may include a semiconductor layer that absorbs X-ray in wavelengths of interest. When an X-ray photon is absorbed in the semiconductor layer, multiple charge carriers (e.g., electrons and holes) are generated and swept under an electric field towards electrical contacts on the semiconductor layer. Cumbersome heat management required in currently available semiconductor X-ray detectors (e.g., Medipix) can make a detector with a large area and a large number of pixels difficult or impossible to produce.

SUMMARY

Disclosed herein is an image sensor comprising: a plurality of X-ray detectors; an actuator configured to move the plurality of X-ray detectors to a plurality of positions, wherein the image sensor is configured to capture, by using the detectors, images of portions of a scene at the positions, respectively, and configured to form an image of the scene by stitching the images of the portions.

According to an embodiment, the plurality of X-ray detectors are spaced apart.

According to an embodiment, the image sensor further comprises a collimator with a plurality of X-ray transmitting zones and an X-ray blocking zone. The X-ray blocking zone is configured to block X-ray that would otherwise incident on a dead zone of the image sensor, and the X-ray transmitting zones are configured to allow at least a portion of X-ray that would incident on active areas of the image sensor.

According to an embodiment, the actuator is configured to move the collimator such that an alignment of the X-ray detectors with the X-ray transmitting zones and the X-ray blocking zone is maintained at the positions.

According to an embodiment, at least some of the plurality of X-ray detectors are arranged in staggered rows.

According to an embodiment, X-ray detectors in a same row are uniform in size; wherein a distance between two neighboring X-ray detectors in a same row is greater than a width of one X-ray detector in the same row in an extending direction of the row and is less than twice that width.

According to an embodiment, active areas of the X-ray detectors tessellate the scene at the positions.

According to an embodiment, the actuator comprises a robotic arm.

According to an embodiment, at least some of the plurality of X-ray detectors comprise multiple layers of detectors.

According to an embodiment, at least some of the plurality of X-ray detectors are rectangular in shape.

According to an embodiment, at least some of the plurality of X-ray detectors are hexagonal in shape.

According to an embodiment, the actuator comprises a control unit configured to determine the positions.

According to an embodiment, at least one of the plurality of X-ray detectors comprises an X-ray absorption layer and an electronics layer; wherein the X-ray absorption layer comprises an electrode; wherein the electronics layer comprises an electronics system; wherein the electronics system comprises: a first voltage comparator configured to compare a voltage of the electrode to a first threshold, a second voltage comparator configured to compare the voltage to a second threshold, a counter configured to register a number of X-ray photons reaching the X-ray absorption layer, and a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, if the second voltage comparator determines that an absolute value of the voltage equals or exceeds an absolute value of the second threshold.

According to an embodiment, the electronics system further comprises a capacitor module electrically connected to the electrode, wherein the capacitor module is configured to collect charge carriers from the electrode.

According to an embodiment, the controller is configured to activate the second voltage comparator at a beginning or expiration of the time delay.

According to an embodiment, the electronics system further comprises a voltmeter, wherein the controller is configured to cause the voltmeter to measure the voltage upon expiration of the time delay.

According to an embodiment, the controller is configured to determine an X-ray photon energy based on a value of the voltage measured upon expiration of the time delay.

According to an embodiment, the controller is configured to connect the electrode to an electrical ground.

According to an embodiment, a rate of change of the voltage is substantially zero at expiration of the time delay.

According to an embodiment, a rate of change of the voltage is substantially non-zero at expiration of the time delay.

Disclosed herein is a system comprising the image sensor described herein and an X-ray source, wherein the system is configured to perform X-ray radiography on human chest or abdomen.

Disclosed herein is a system comprising the image sensor described herein and an X-ray source, wherein the system is configured to perform X-ray radiography on human mouth.

Disclosed herein is a cargo scanning or non-intrusive inspection (NII) system, comprising the image sensor described herein and an X-ray source, wherein the cargo scanning or non-intrusive inspection (NII) system is configured to form an image using backscattered X-ray.

Disclosed herein is a cargo scanning or non-intrusive inspection (NII) system, comprising the image sensor described herein and an X-ray source, wherein the cargo scanning or non-intrusive inspection (NII) system is configured to form an image using X-ray transmitted through an object inspected.

Disclosed herein is a full-body scanner system comprising the image sensor described herein and an X-ray source.

Disclosed herein is an X-ray computed tomography (X-ray CT) system comprising the image sensor described herein and an X-ray source.

Disclosed herein is an electron microscope comprising the image sensor described herein, an electron source and an electronic optical system.

Disclosed herein is a system comprising the image sensor described herein, wherein the system is an X-ray telescope, or an X-ray microscopy, or wherein the system is configured to perform mammography, industrial defect detection, microradiography, casting inspection, weld inspection, or digital subtraction angiography.

Disclosed herein is a method of forming an image of a scene using an image sensor comprising a plurality of X-ray detectors, the method comprising: taking a first image of a first portion of the scene by positioning the X-ray detectors to a first position; taking a second image of a second portion of the scene by positioning the X-ray detectors to a second position; forming the image of the scene by stitching at least the first image and the second image.

According to an embodiment, the first and the second images have a spatial overlap.

According to an embodiment, the image sensor further comprises a collimator; wherein the method further comprises positioning the collimator before taking the first and the second images.

BRIEF DESCRIPTION OF FIGURES

FIG. 4A schematically shows a top view of a package including the detector and a printed circuit board (PCB).

FIG. 4B schematically shows a cross-sectional view of an image sensor, where a plurality of the packages of FIG. 4A are mounted to another PCB.

FIG. 5 schematically shows a functional block diagram of an image sensor, according to an embodiment.

FIG. 7 schematically shows an image sensor taking a series of images of a scene, according to an embodiment.

DETAILED DESCRIPTION

Figure 1A:
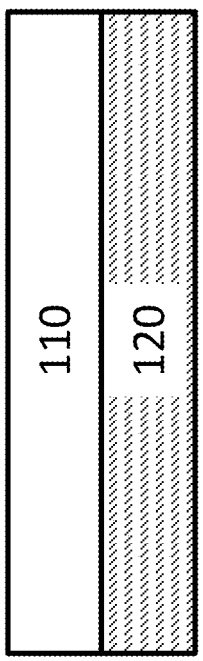
FIG. 1A schematically shows a cross-sectional view of an X-ray detector, according to an embodiment.

FIG. 1A schematically shows a cross-sectional view of the detector 100, according to an embodiment. The detector 100 may include an X-ray absorption layer 110 and an electronics layer 120 (e.g., an ASIC) for processing or analyzing electrical signals incident X-ray generates in the X-ray absorption layer 110. In an embodiment, the detector 100 does not comprise a scintillator. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest.

Figure 1B:
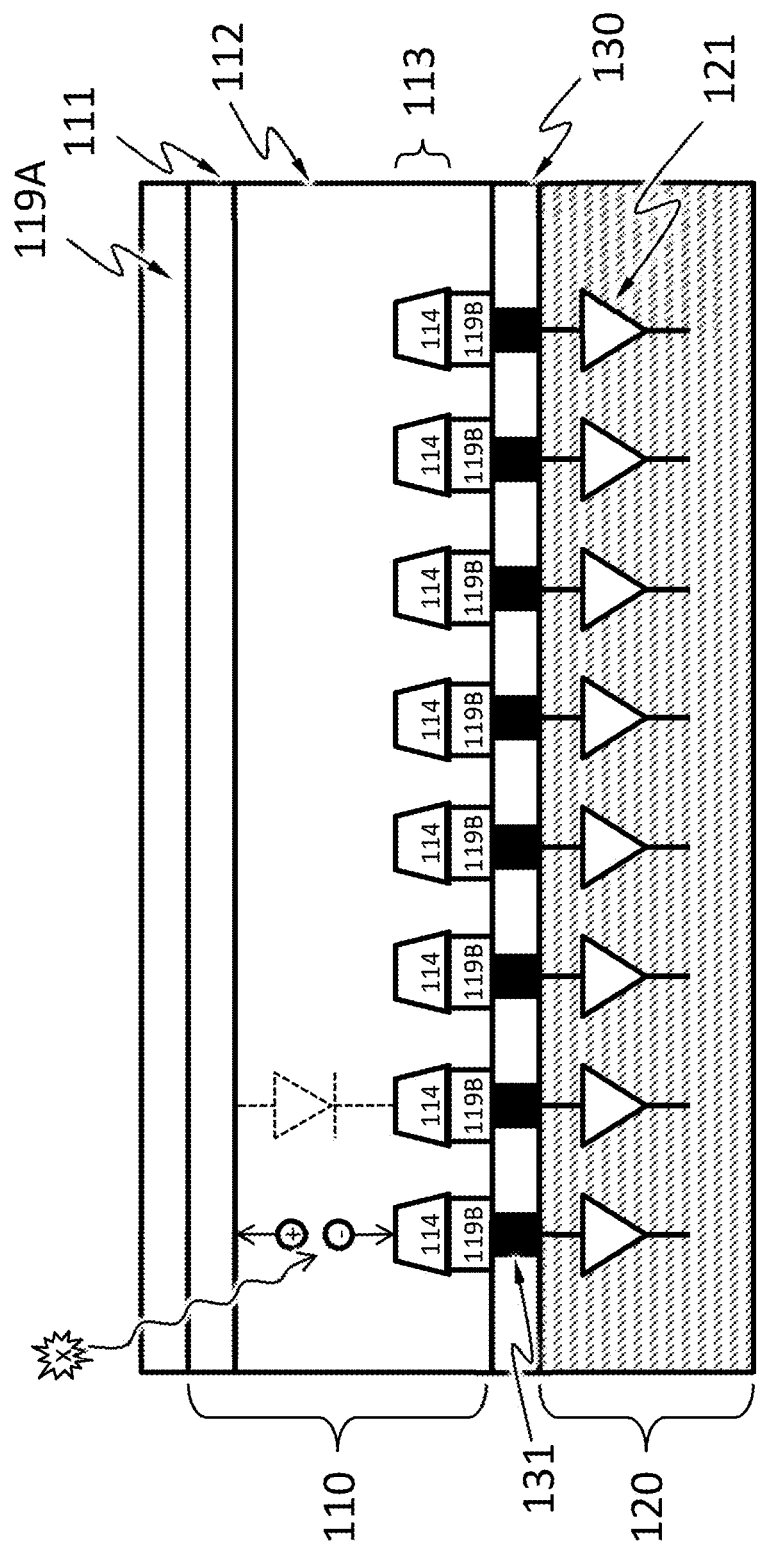
FIG. 1B schematically shows a detailed cross-sectional view of the detector, according to an embodiment.

As shown in a detailed cross-sectional view of the detector 100 in FIG. 1B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 1B, each of the discrete regions 114 of the second doped region 113 forms a diode with the first doped region 111 and the optional intrinsic region 112. Namely, in the example in FIG. 1B, the X-ray absorption layer 110 has a plurality of diodes having the first doped region 111 as a shared electrode. The first doped region 111 may also have discrete portions.

When an X-ray photon hits the X-ray absorption layer 110 including diodes, the X-ray photon may be absorbed and generate one or more charge carriers by a number of mechanisms. An X-ray photon may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single X-ray photon are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by an X-ray photon incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by an X-ray photon incident therein flow to the discrete region 114. Namely, less than 2%, less than 1%, less than 0.1%, or less than 0.01% of these charge carriers flow beyond the pixel.

Figure 1C:
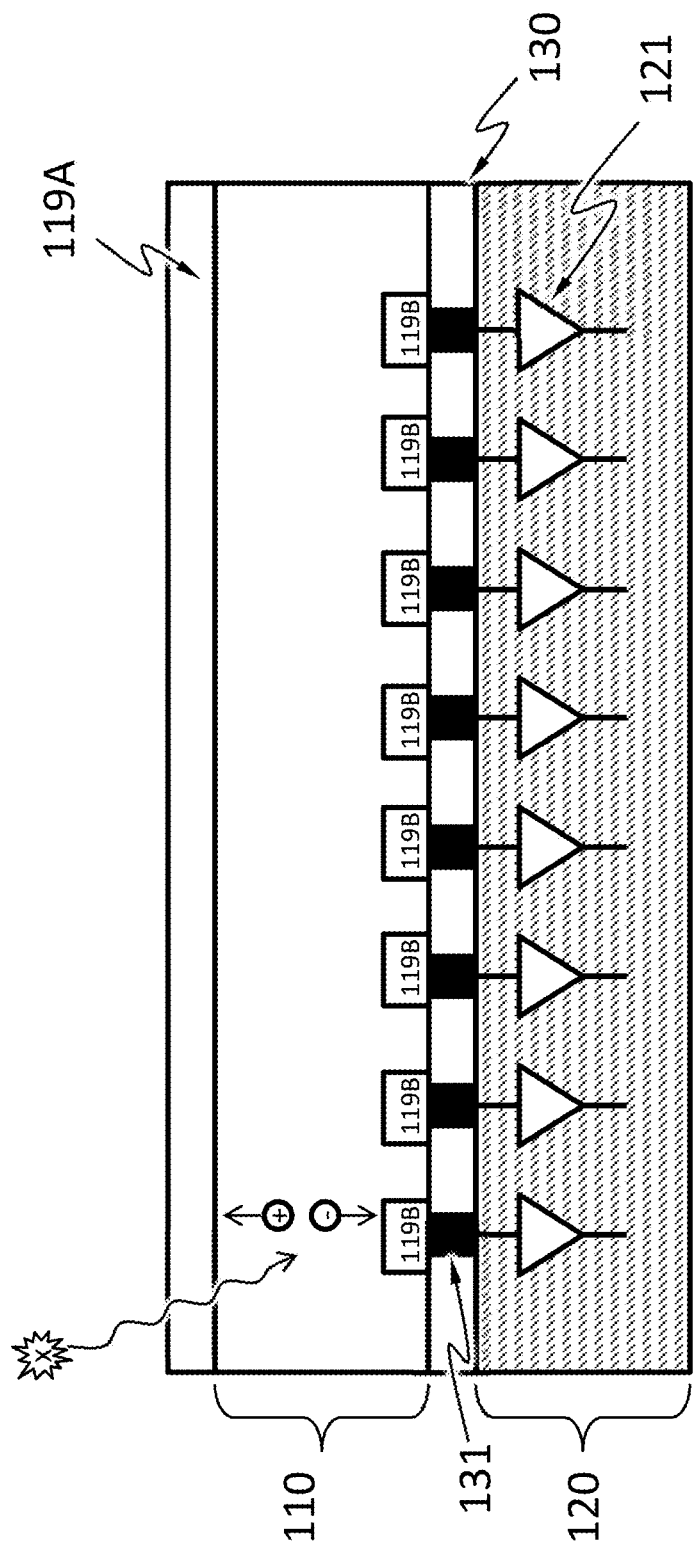
FIG. 1C schematically shows an alternative detailed cross-sectional view of the detector, according to an embodiment.

As shown in an alternative detailed cross-sectional view of the detector 100 in FIG. 1C, according to an embodiment, the X-ray absorption layer 110 may include a resistor of a semiconductor material such as, silicon, germanium, GaAs, CdTe, CdZnTe, or a combination thereof, but does not include a diode. The semiconductor may have a high mass attenuation coefficient for the X-ray energy of interest.

When an X-ray photon hits the X-ray absorption layer 110 including a resistor but not diodes, it may be absorbed and generate one or more charge carriers by a number of mechanisms. An X-ray photon may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single X-ray photon are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by an X-ray photon incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by an X-ray photon incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by X-ray photons incident on the X-ray absorption layer 110. The electronic system 121 may include an analog circuitry such as a filter network, amplifiers, integrators, and comparators, or a digital circuitry such as a microprocessors, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

Figure 2:
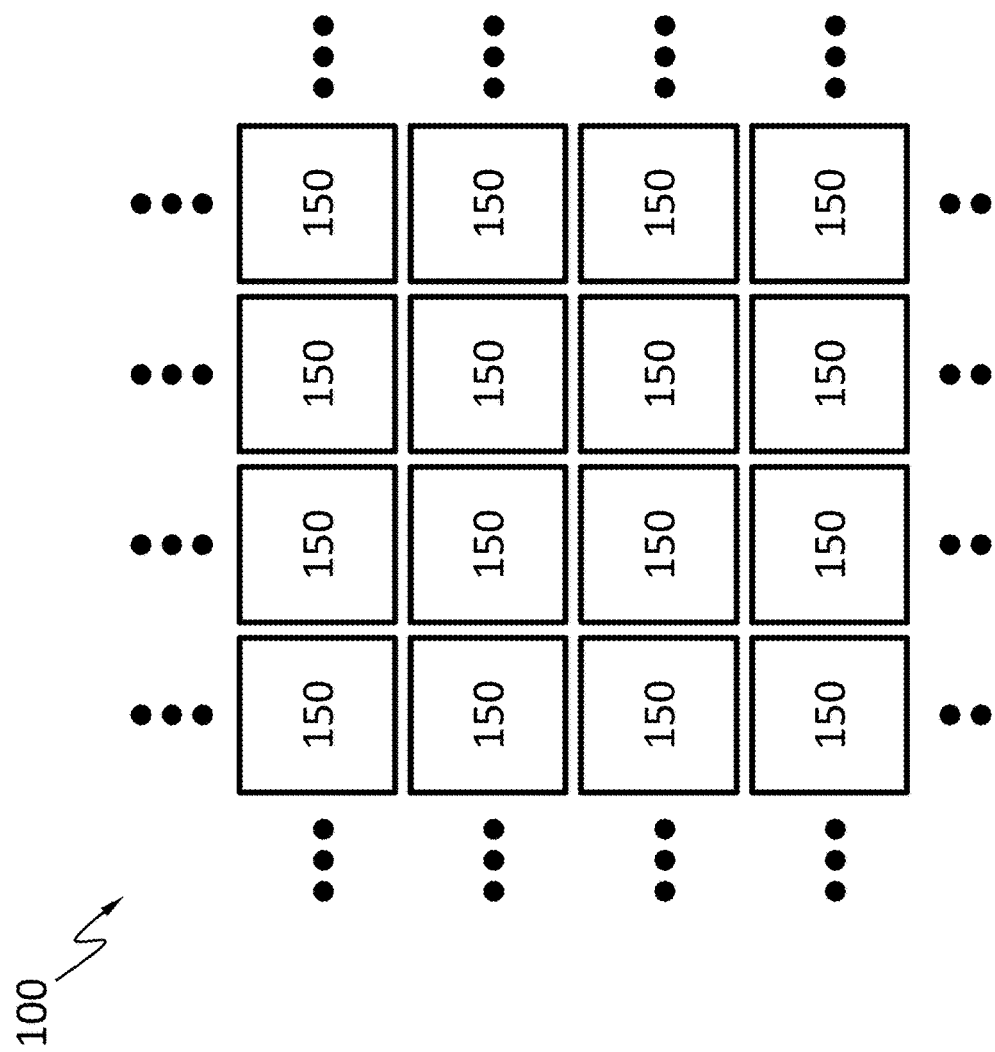
FIG. 2 schematically shows that the device may have an array of pixels, according to an embodiment.

FIG. 2 schematically shows that the detector 100 may have an array of pixels 150. The array may be a rectangular array, a honeycomb array, a hexagonal array or any other suitable array. Each pixel 150 may be configured to detect an X-ray photon incident thereon, measure the energy of the X-ray photon, or both. For example, each pixel 150 may be configured to count numbers of X-ray photons incident thereon whose energy falls in a plurality of bins, within a period of time. All the pixels 150 may be configured to count the numbers of X-ray photons incident thereon within a plurality of bins of energy within the same period of time. Each pixel 150 may have its own analog-to-digital converter (ADC) configured to digitize an analog signal representing the energy of an incident X-ray photon into a digital signal. The ADC may have a resolution of 10 bits or higher. Each pixel 150 may be configured to measure its dark current, such as before or concurrently with each X-ray photon incident thereon. Each pixel 150 may be configured to deduct the contribution of the dark current from the energy of the X-ray photon incident thereon. The pixels 150 may be configured to operate in parallel. For example, when one pixel 150 measures an incident X-ray photon, another pixel 150 may be waiting for an X-ray photon to arrive. The pixels 150 may be but do not have to be individually addressable.

Figure 3:
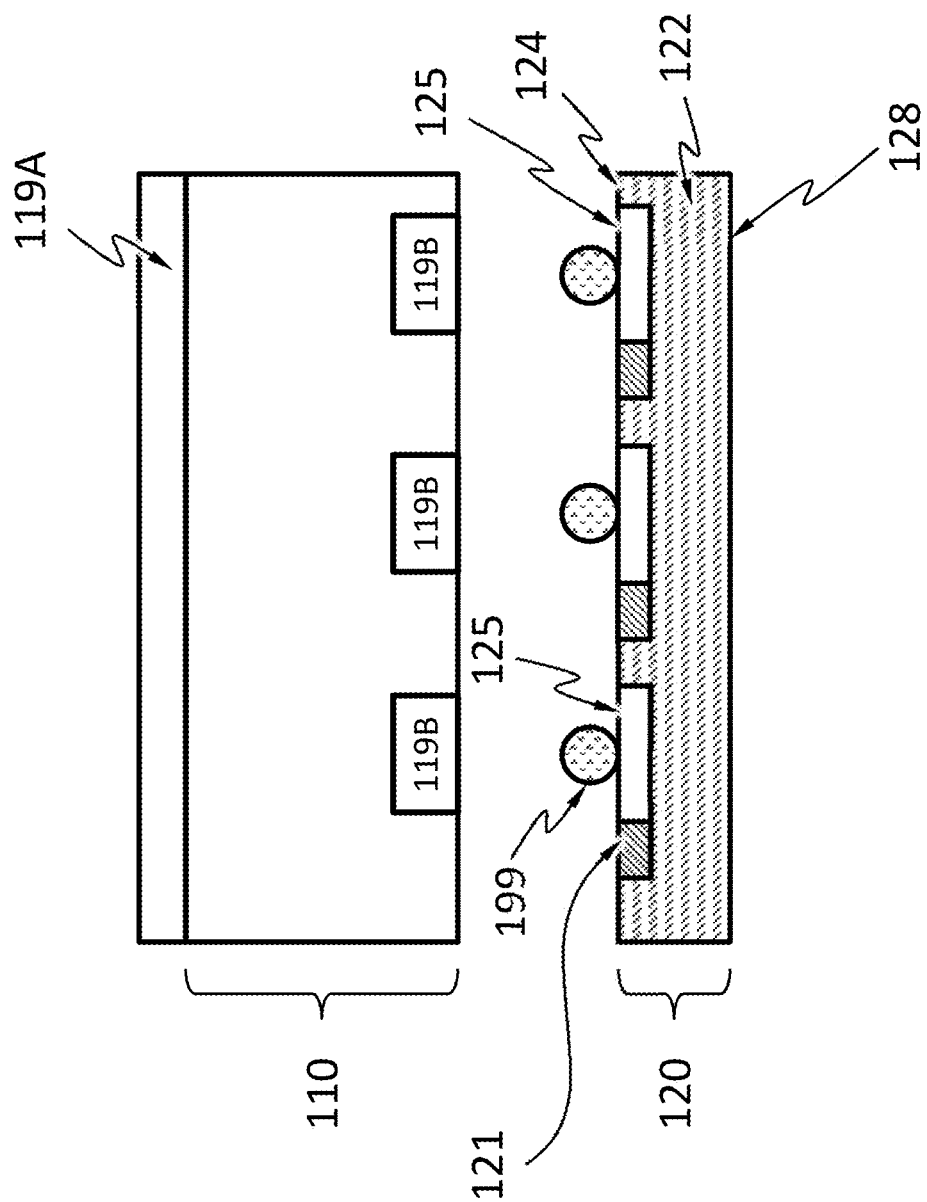
FIG. 3 schematically shows a cross-sectional view of an electronics layer in the detector, according to an embodiment.

FIG. 3 schematically shows the electronics layer 120 according to an embodiment. The electronic layer 120 comprises a substrate 122 having a first surface 124 and a second surface 128. A "surface" as used herein is not necessarily exposed, but can be buried wholly or partially. The electronic layer 120 comprises one or more electric contacts 125 on the first surface 124. The one or more electric contacts 125 may be configured to be electrically connected to one or more electrical contacts 119B of the X-ray absorption layer 110. The electronics system 121 may be in or on the substrate 122.

The substrate 122 may be a thinned substrate. For example, the substrate may have at thickness of 750 microns or less, 200 microns or less, 100 microns or less, 50 microns or less, 20 microns or less, or 5 microns or less. The substrate 122 may be a silicon substrate or a substrate or other suitable semiconductor or insulator. The substrate 122 may be produced by grinding a thicker substrate to a desired thickness.

The one or more electric contacts 125 may be a layer of metal or doped semiconductor. For example, the electric contacts 125 may be gold, copper, platinum, palladium, doped silicon, etc.

FIG. 3 schematically shows bonding between the X-ray absorption layer 110 and the electronic layer 120 at the electrical contact 119B of the X-ray absorption layer 110 and electrical contacts 125 of the electronic layer 120. The bonding may be by a suitable technique such as direct bonding or flip chip bonding.

Direct bonding is a wafer bonding process without any additional intermediate layers (e.g., solder bumps). The bonding process is based on chemical bonds between two surfaces. Direct bonding may be at elevated temperature but not necessarily so.

Flip chip bonding uses solder bumps 199 deposited onto contact pads (e.g., the electrical contact 119B of the X-ray absorption layer 110 or the electrical contacts 125). Either the X-ray absorption layer 110 or the electronic layer 120 is flipped over and the electrical contact 119B of the X-ray absorption layer 110 are aligned to the electrical contacts 125. The solder bumps 199 may be melted to solder the electrical contact 119B and the electrical contacts 125 together. Any void space among the solder bumps 199 may be filled with an insulating material.

FIG. 4A schematically shows a top view of a package 200 including the detector 100 and a printed circuit board (PCB) 400. The term "PCB" as used herein is not limited to a particular material. For example, a PCB may include a semiconductor. The detector 100 is mounted to the PCB 400. The wiring between the detector 100 and the PCB 400 is not shown for the sake of clarity. The PCB 400 may have one or more detectors 100. The PCB 400 may have an area not covered by the detector 100 (e.g., for accommodating bonding wires 410). The detector 100 may have an active area 190, which is where the pixels 150 are located. The detector 100 may have a perimeter zone 195 near the edges of the detector 100. The perimeter zone 195 has no pixels and the detector 100 does not detect photons incident on the perimeter zone 195.

The package 200 may be mounted to a system PCB 450. The electrical connection between the PCBs 400 in the packages 200 and the system PCB 450 may be made by bonding wires 410. In order to accommodate the bonding wires 410 on the PCB 400, the PCB 400 has an area 405 not covered by the detector 100. In order to accommodate the bonding wires 410 on the system PCB 450, the packages 200 have gaps in between. The gaps may be approximately 1 mm or more. Light incident on the perimeter zones 195, on the area 405 or on the gaps cannot be detected by the packages 200 on the system PCB 450. A dead zone of a detector is the area of the photon-receiving surface of the detector, in which incident photons cannot be detected by the detector. A dead zone of a package (e.g., package 200) is the area of the photon-receiving surface of the package, in which incident photons cannot be detected by the detector or detectors in the package. In this example shown in FIG. 4A, the dead zone of the package 200 includes the perimeter zones 195 and the area 405. A dead zone (e.g., 488) of an image sensor with a group of packages (e.g., packages mounted on the same PCB, packages arranged in the same layer) includes the combination of the dead zones of the packages in the group and the gaps among the packages.

In order to capture the light incident in the dead zone 488 of a layer of the packages, the packages 200 may be arranged in multiple layers, where the packages 200 are arranged such that light incident on the dead zone 488 of one layer is captured by the packages 200 in another layer. Multiple layers of packages would lead to higher cost.

An image sensor including the detectors 100 may have a dead zone. If the image sensor captures images of multiple portions of a scene, the images of the portions may be stitched to for an image of the entire scene. As shown in FIG. 5, according to an embodiment, an image sensor 9000 comprises plurality of X-ray detectors 100 (which may be part of a plurality of packages) as described above, an optional collimator 200 and an actuator 500. The actuator 500 may include a control unit 600. In some embodiments, the collimator 200 may be omitted. The actuator 500 is configured to move the detectors 100 and the optional collimator 200 to multiple positions. The positions may be determined by the control unit 600. The positions may be selected such that the active areas of the detectors 100 collectively tessellate the entire scene at the multiple positions.

Figure 6:
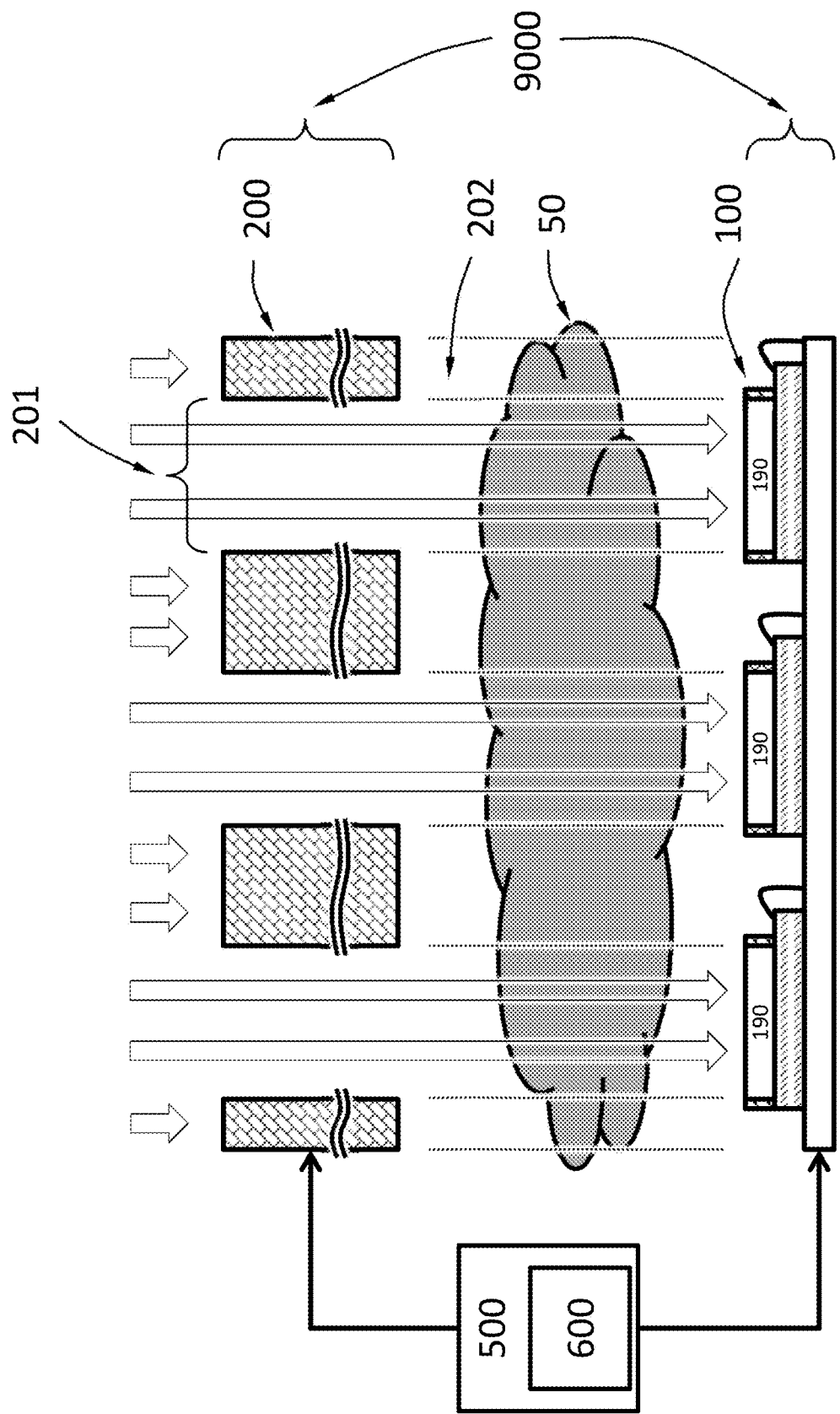
FIG. 6 schematically shows an image sensor comprising a plurality of X-ray detectors and a collimator, being used to take an image of a scene, according to an embodiment.

FIG. 6 schematically shows the image sensor 9000 being used for taking an image of a portion of a scene 50, according to an embodiment. The actuator 500 may move the X-ray detectors 100 to a plurality of positions (e.g., under control by the control unit 600). At each of the positions, the image sensor 9000 takes an image of a portion of the scene 50. The images of the portions are then stitched to form an image of the scene 50. The images of the portions may have overlap among one another to facilitate stitching.

The optional collimator 200 may be configured such that it prevents X-ray that would incident on the dead zone of the image sensor 9000 from reaching the object being imaged. The optional collimator 200 may have a plurality of X-ray transmitting zones 201 and an X-ray blocking zone 202. The X-ray blocking zone 202 blocks X-ray that would otherwise incident on the dead zone of the image sensor 9000, and the X-ray transmitting zones 201 allow at least a portion of X-ray that would incident on active areas of the image sensor 9000 to pass. The X-ray blocking zone 202 may be aligned with the dead zone of the image sensor. When the actuator 500 moves the image sensor 9000, the optional collimator 200 and the detectors 100 may be moved together (i.e., without relative movement).

According to an embodiment, the collimator 200 may be a metal sheet with a thickness enough for blocking X-ray transmission with holes in the metal sheet. The holes may function as the X-ray transmitting zones 201 and the rest of the metal sheet may function as the X-ray blocking zone 202. The size and arrangement of the holes may be the same as those of the active areas of the X-ray detectors 100 on the image sensor 9000.

According to an embodiment, the actuator 500 is configured to move the collimator 200 and the detectors 100 such that the alignment between the detectors 100 with the collimator 200 is maintained at each of the positions where images of the portions of the scene 50 are captured. As each of the positions, the incident X-ray that would otherwise incident on the dead zone of the image sensor 9000 is blocked by the X-ray blocking zone 202 of the collimator 200. The actuator 500 may have various designs. For example, actuator 500 may be a robotic arm that connects to the system PCB 450 and move the X-ray detectors 100 with the system PCB 450.

As shown in FIG. 7, according to an embodiment, at least some of the X-ray detectors 100 of the image sensor 9000 are arranged in an array. To form an image of the scene 50, the actuator 500 moves the X-ray detectors 100 to multiple positions (e.g., A, B and C in FIG. 7) relative the scene 50, where the image sensor 9000 captures images (e.g., 51A, 51B and 51C) of portions of the scene at these positions, respectively. Every point of the scene 50 is in at least one image of a portion. Namely, the images of the portions when stitched together cover the entire scene 50. The images of the portions may have overlaps among them to facilitate stitching.

The detectors 100 may be arranged in a variety of ways in the image sensor 9000. FIG. 8A schematically shows one arrangement, according to an embodiment, where the detectors 100 are arranged in staggered rows. For example, detectors 100A and 100B are in the same row, aligned in the Y direction, and uniform in size; detectors 100C and 100D are in the same row, aligned in the Y direction, and uniform in size. Detectors 100A and 100B are staggered in the X direction with respect to detectors 100C and 100D. According to an embodiment, a distance X2 between two neighboring X-ray detectors 100A and 100B in the same row is greater than a width X1 (i.e., dimension in the X direction, which is the extending direction of the row) of one X-ray detector in the same row and is less than twice the width X1. Detectors 100A and 100E are in a same column, aligned in the X direction, and uniform in size; a distance Y2 between two neighboring X-ray detectors 100A and 100E in the same column is less than a width Y1 (i.e., dimension in the Y direction) of one X-ray detector in the same column. This arrangement allows imaging of the scene as shown in FIG. 7, and an image of the scene may be obtain from stitching three images of portions of the scene captured at three positions spaced apart in the X direction.

Figure 8B:
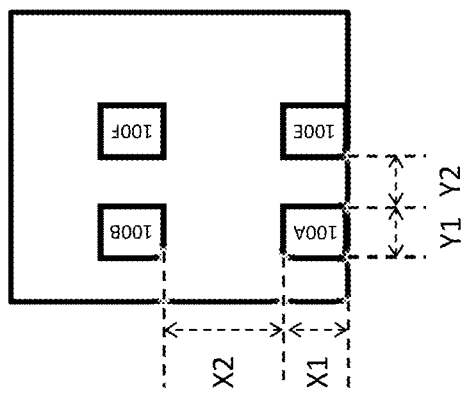
FIG. 8A-8C schematically show arrangements of the detectors in an image sensor, according to some embodiments.
Figure 8A:
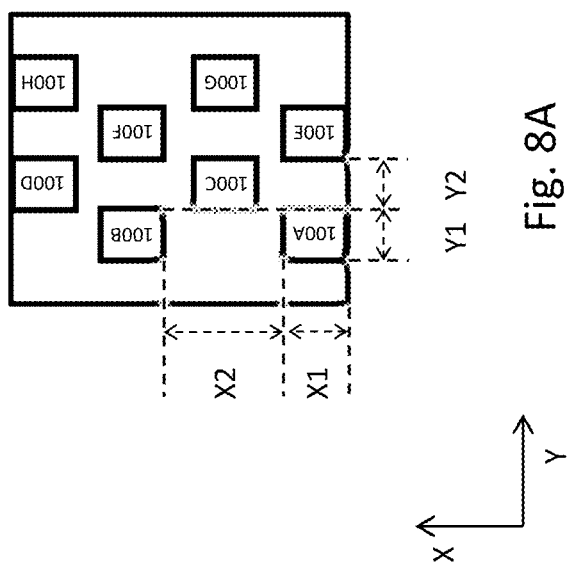

FIG. 8B schematically shows another arrangement, according to an embodiment, where the detectors 100 are arranged in a rectangular grid. For example, the detectors 100 may include detectors 100A, 100B, 100E and 100F as arranged exactly in FIG. 8A, without detectors 100C, 100D, 100G, or 100H in FIG. 8A. This arrangement allows imaging of the scene by taking images of portions of the scene at six positions. For example, three positions spaced apart in the X direction and another three positions spaced apart in the X direction and spaced apart in the Y direction from the first three positions.

Figure 8C:
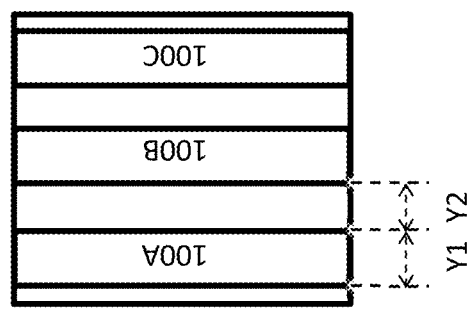

Other arrangements may also be possible. For example, in FIG. 8C, the detectors 100 may span the whole width of the image sensor 9000 in the X-direction, with a distance Y2 between two neighboring detectors 100 being less than a width of one X-ray detector Y1. Assuming the width of the detectors in the X direction is greater than the width of the scene in the X direction, the image of the scene may be stitched from two images of portions of the scene captured at two positions spaced apart in the Y direction.

Figure 9:
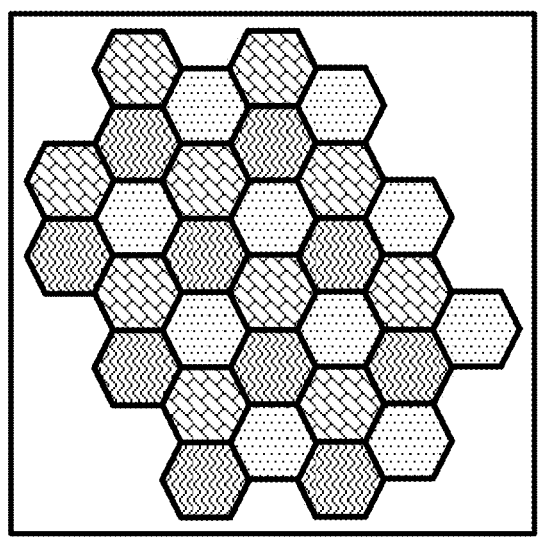
FIG. 9 schematically shows an image sensor with plurality of detectors that are hexagonal in shape, according to an embodiment.

The X-ray detectors describe above may be provided with any suitable size and shapes. According to an embodiment (e.g., in FIG. 7), at least some of the X-ray detectors are rectangular in shape. According to an embodiment, as shown in FIG. 9, at least some of the X-ray detectors are hexagonal in shape. In such X-ray detectors, the X-ray detectors and the corresponding collimators that are aligned may have the same shape.

As discussed, a method of obtaining an image of a scene using an image sensor described above comprises: taking a first image of a first portion of the scene by positioning the X-ray detectors to a first position; taking a second image of a second portion of the scene by positioning the X-ray detectors to a second position; forming the image of the scene by stitching at least the first image and the second image.

According to an embodiment, the first and the second images have a spatial overlap.

According to an embodiment, the image sensor further comprises a collimator; wherein the method further comprises positioning the collimator before taking the first and the second images.

The image sensor described above may be used in various system such as those provided below.

Figure 10:
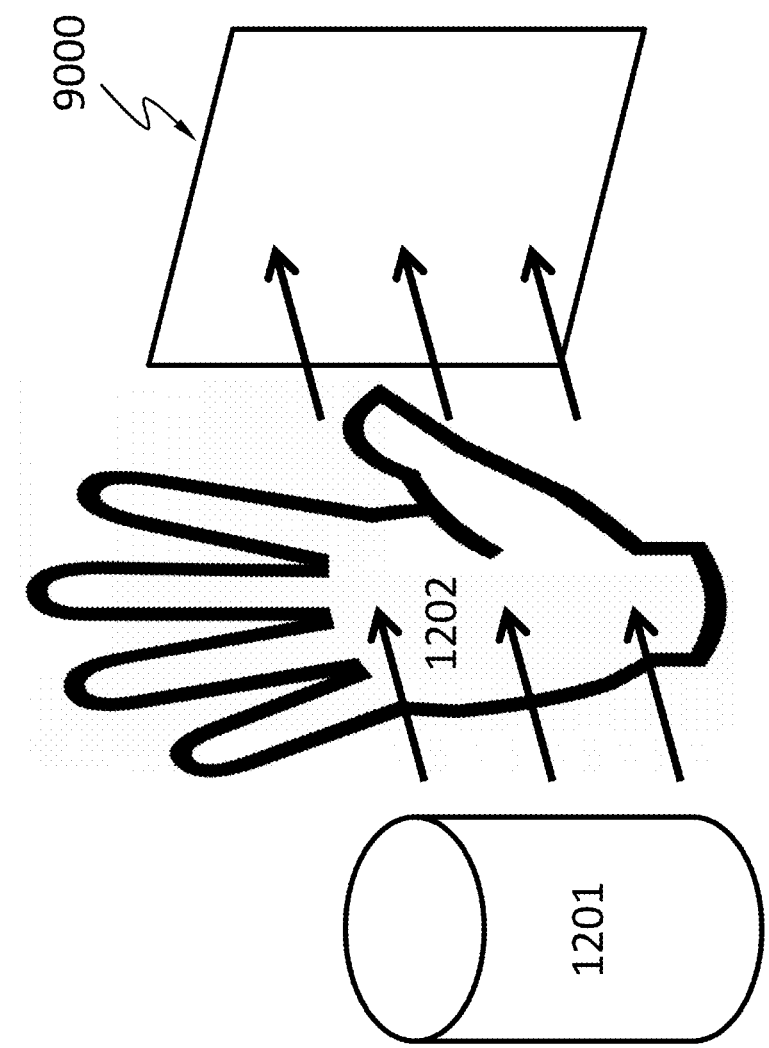
FIG. 10 schematically shows a system comprising the image sensor described herein, suitable for medical imaging such as chest X-ray radiography, abdominal X-ray radiography, etc., according to an embodiment FIG. 11 schematically shows a system comprising the image sensor described herein suitable for dental X-ray radiography, according to an embodiment.

FIG. 10 schematically shows a system comprising an image sensor 9000 as described in relation to FIG. 4A-FIG. 9. The system may be used for medical imaging such as chest X-ray radiography, abdominal X-ray radiography, etc. The system comprises an X-ray source 1201. X-ray emitted from the X-ray source 1201 penetrates an object 1202 (e.g., a human body part such as chest, limb, abdomen), is attenuated by different degrees by the internal structures of the object 1202 (e.g., bones, muscle, fat and organs, etc.), and is projected to the image sensor 9000. The image sensor 9000 forms an image by detecting the intensity distribution of the X-ray.

Figure 11:
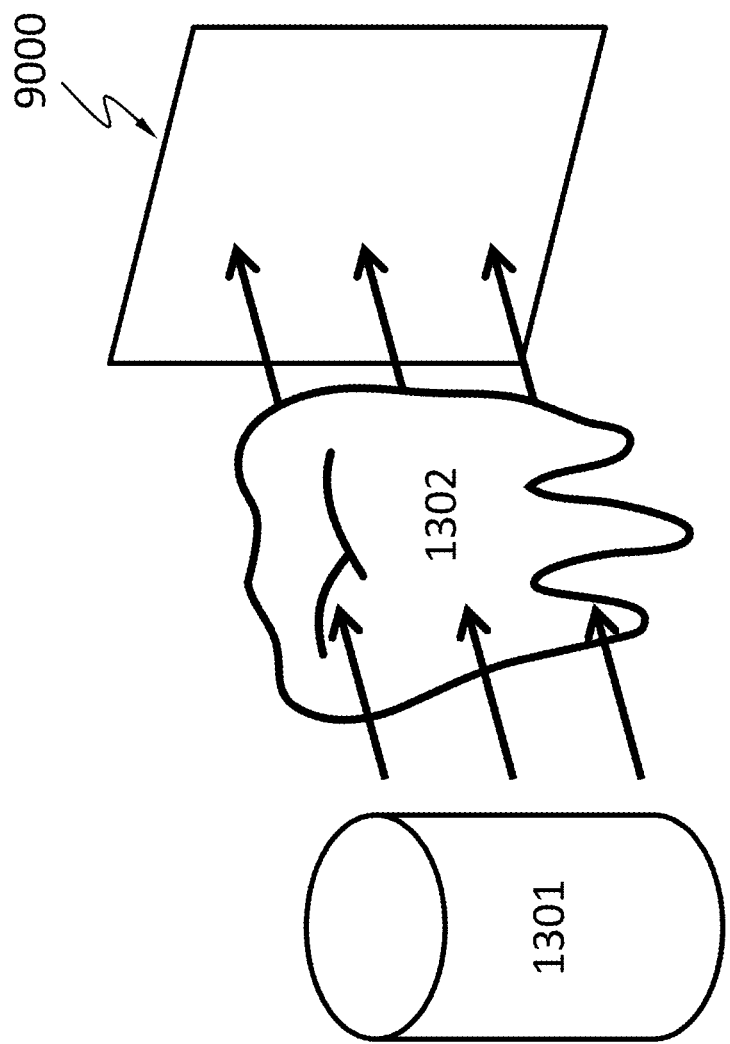

FIG. 11 schematically shows a system comprising an image sensor 9000 as described in relation to FIG. 4A-FIG. 9. The system may be used for medical imaging such as dental X-ray radiography. The system comprises an X-ray source 1301. X-ray emitted from the X-ray source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the image sensor 9000. The image sensor 9000 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

Figure 12:
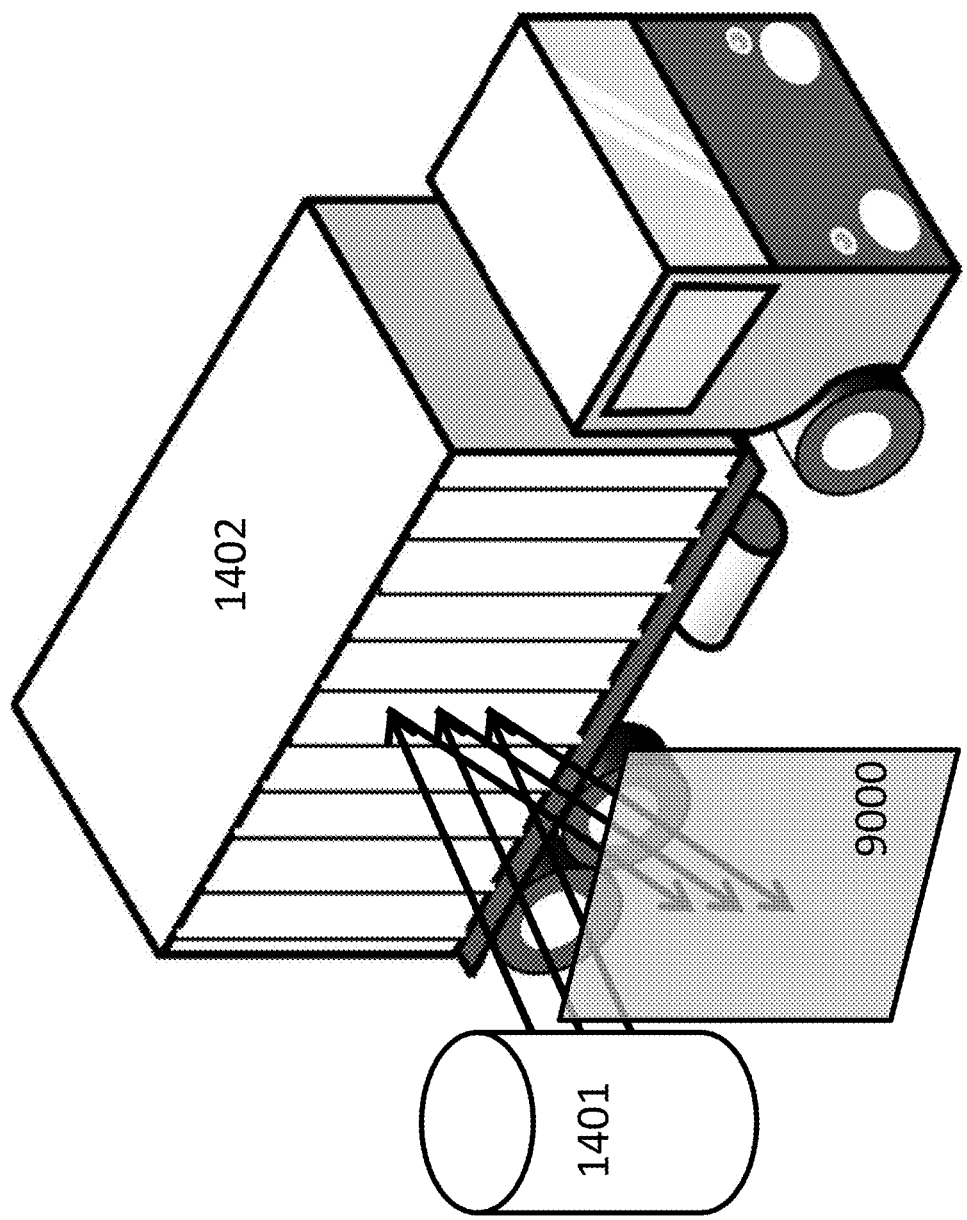
FIG. 12 schematically shows a cargo scanning or non-intrusive inspection (NII) system comprising the image sensor described herein, according to an embodiment.

FIG. 12 schematically shows a cargo scanning or non-intrusive inspection (NII) system comprising an image sensor 9000 as described in relation to FIG. 4A-FIG. 9. The system may be used for inspecting and identifying goods in transportation systems such as shipping containers, vehicles, ships, luggage, etc. The system comprises an X-ray source 1401. X-ray emitted from the X-ray source 1401 may backscatter from an object 1402 (e.g., shipping containers, vehicles, ships, etc.) and be projected to the image sensor 9000. Different internal structures of the object 1402 may backscatter X-ray differently. The image sensor 9000 forms an image by detecting the intensity distribution of the backscattered X-ray and/or energies of the backscattered X-ray photons.

Figure 13:
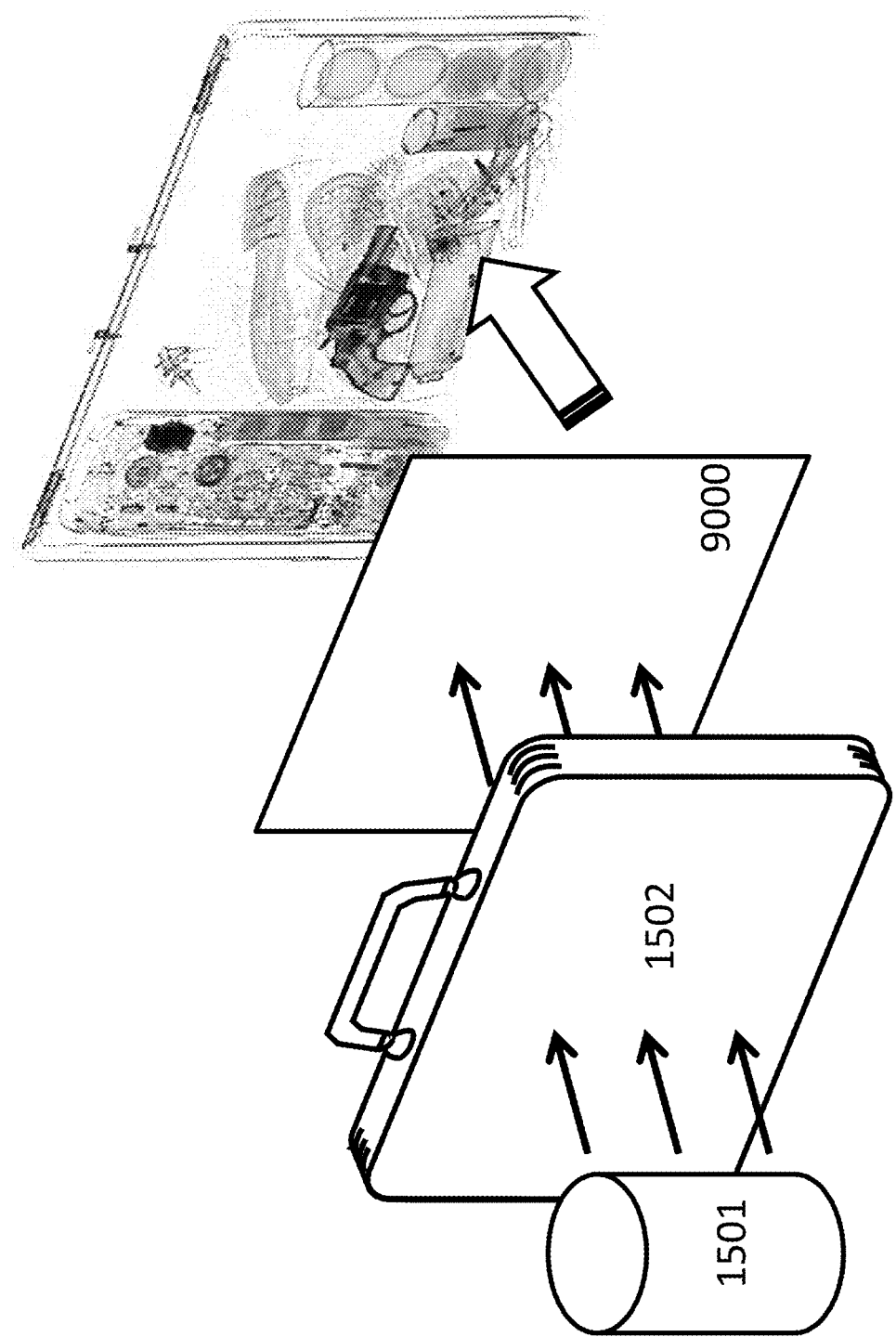
FIG. 13 schematically shows another cargo scanning or non-intrusive inspection (NII) system comprising the image sensor described herein, according to an embodiment.

FIG. 13 schematically shows another cargo scanning or non-intrusive inspection (NII) system comprising an image sensor 9000 as described in relation to FIG. 4A-FIG. 9. The system may be used for luggage screening at public transportation stations and airports. The system comprises an X-ray source 1501. X-ray emitted from the X-ray source 1501 may penetrate a piece of luggage 1502, be differently attenuated by the contents of the luggage, and projected to the image sensor 9000. The image sensor 9000 forms an image by detecting the intensity distribution of the transmitted X-ray. The system may reveal contents of luggage and identify items forbidden on public transportation, such as firearms, narcotics, edged weapons, flammables.

Figure 14:
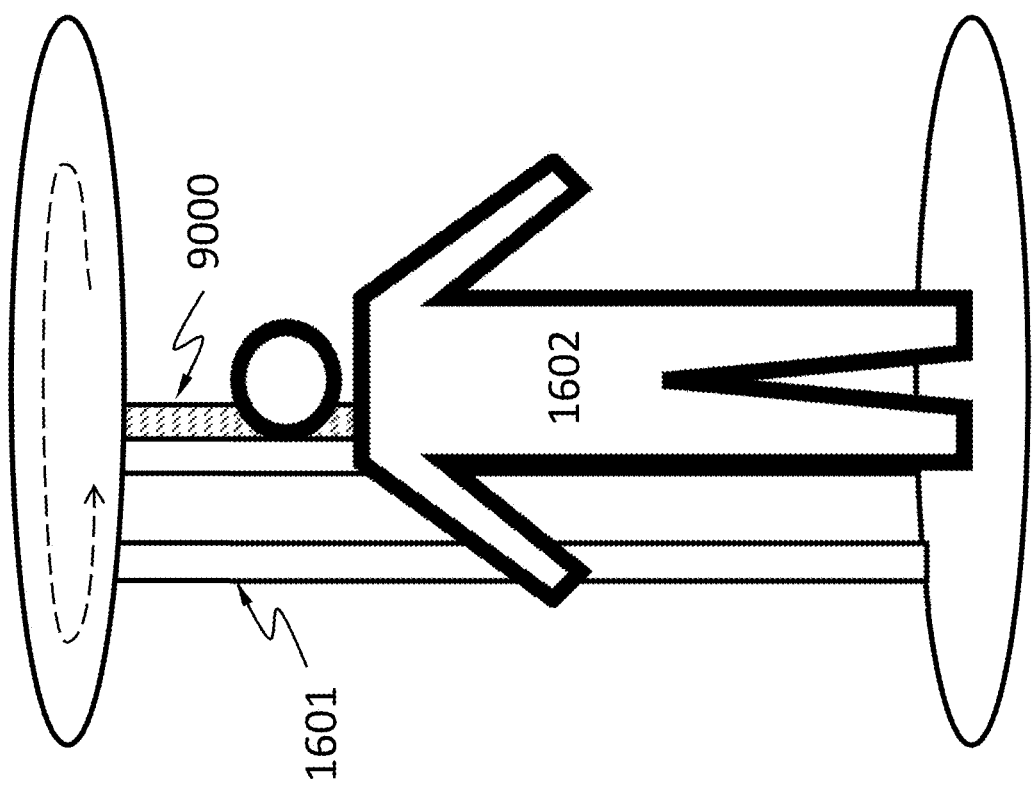
FIG. 14 schematically shows a full-body scanner system comprising the image sensor described herein, according to an embodiment.

FIG. 14 schematically shows a full-body scanner system comprising an image sensor 9000 as described in relation to FIG. 4A-FIG. 9. The full-body scanner system may detect objects on a person's body for security screening purposes, without physically removing clothes or making physical contact. The full-body scanner system may be able to detect non-metal objects. The full-body scanner system comprises an X-ray source 1601. X-ray emitted from the X-ray source 1601 may backscatter from a human 1602 being screened and objects thereon, and be projected to the image sensor 9000. The objects and the human body may backscatter X-ray differently. The image sensor 9000 forms an image by detecting the intensity distribution of the backscattered X-ray. The image sensor 9000 and the X-ray source 1601 may be configured to scan the human in a linear or rotational direction.

Figure 15:
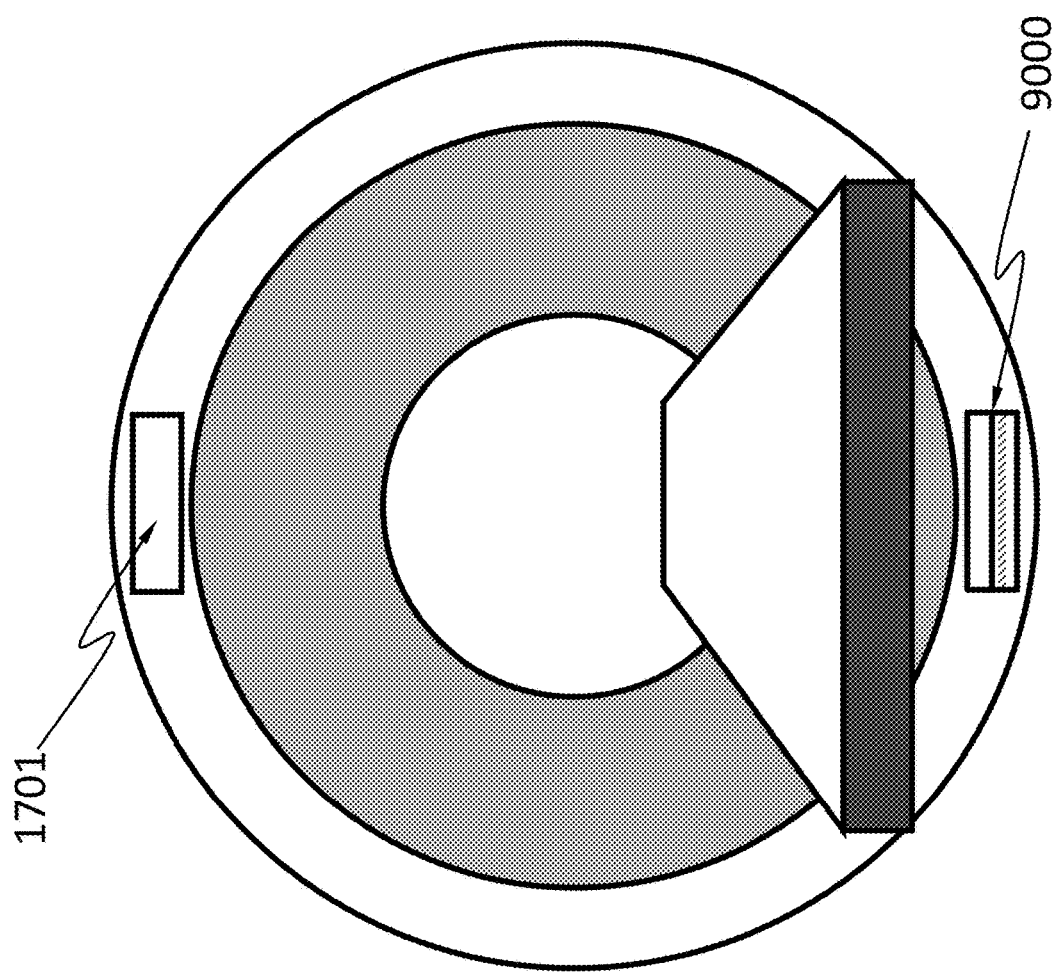
FIG. 15 schematically shows an X-ray computed tomography (X-ray CT) system comprising the image sensor described herein, according to an embodiment.

FIG. 15 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises an image sensor 9000 as described in relation to FIG. 4A-FIG. 9 and an X-ray source 1701. The image sensor 9000 and the X-ray source 1701 may be configured to rotate synchronously along one or more circular or spiral paths.

Figure 16:
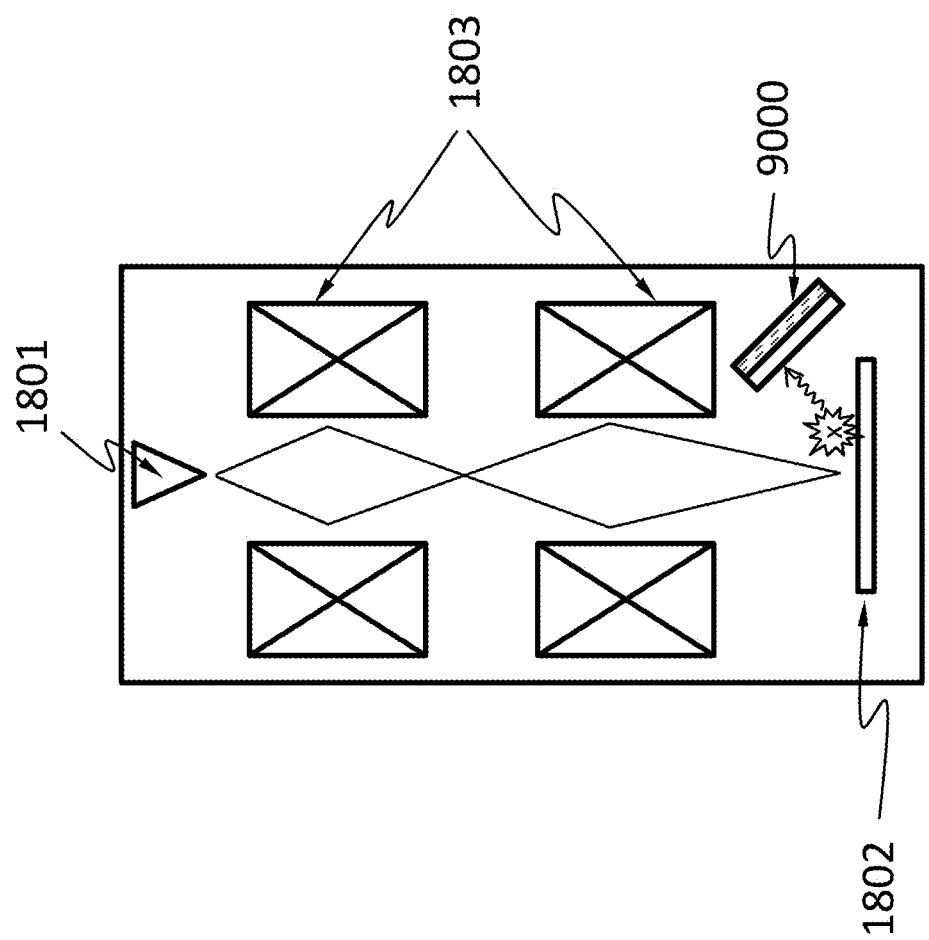
FIG. 16 schematically shows an electron microscope comprising the image sensor described herein, according to an embodiment.

FIG. 16 schematically shows an electron microscope. The electron microscope comprises an electron source 1801 (also called an electron gun) that is configured to emit electrons. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise an image sensor 9000 as described in relation to FIG. 4A-FIG. 9, for performing energy-dispersive X-ray spectroscopy (EDS). EDS is an analytical technique used for the elemental analysis or chemical characterization of a sample. When the electrons incident on a sample, they cause emission of characteristic X-rays from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the image sensor 9000.

The image sensor 9000 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this image sensor 9000 in place of a photographic plate, a photographic film, a PSP plate, an X-ray image intensifier, a scintillator, or another semiconductor X-ray detector.

Figure 17A:
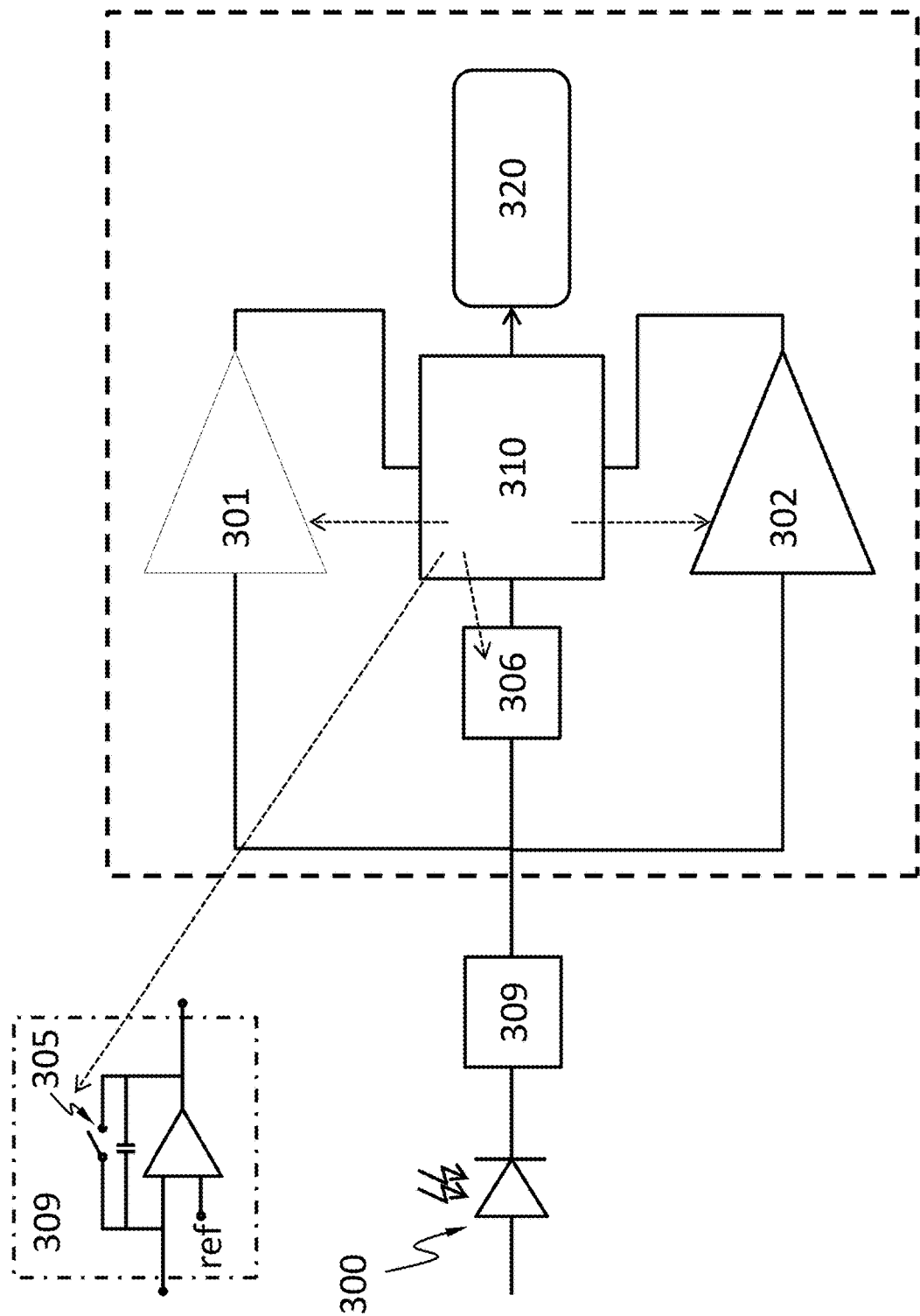
FIG. 17A and FIG. 17B each show a component diagram of an electronic system of the detector in FIG. 1A, FIG. 1B and FIG. 1C, according to an embodiment.
Figure 17B:
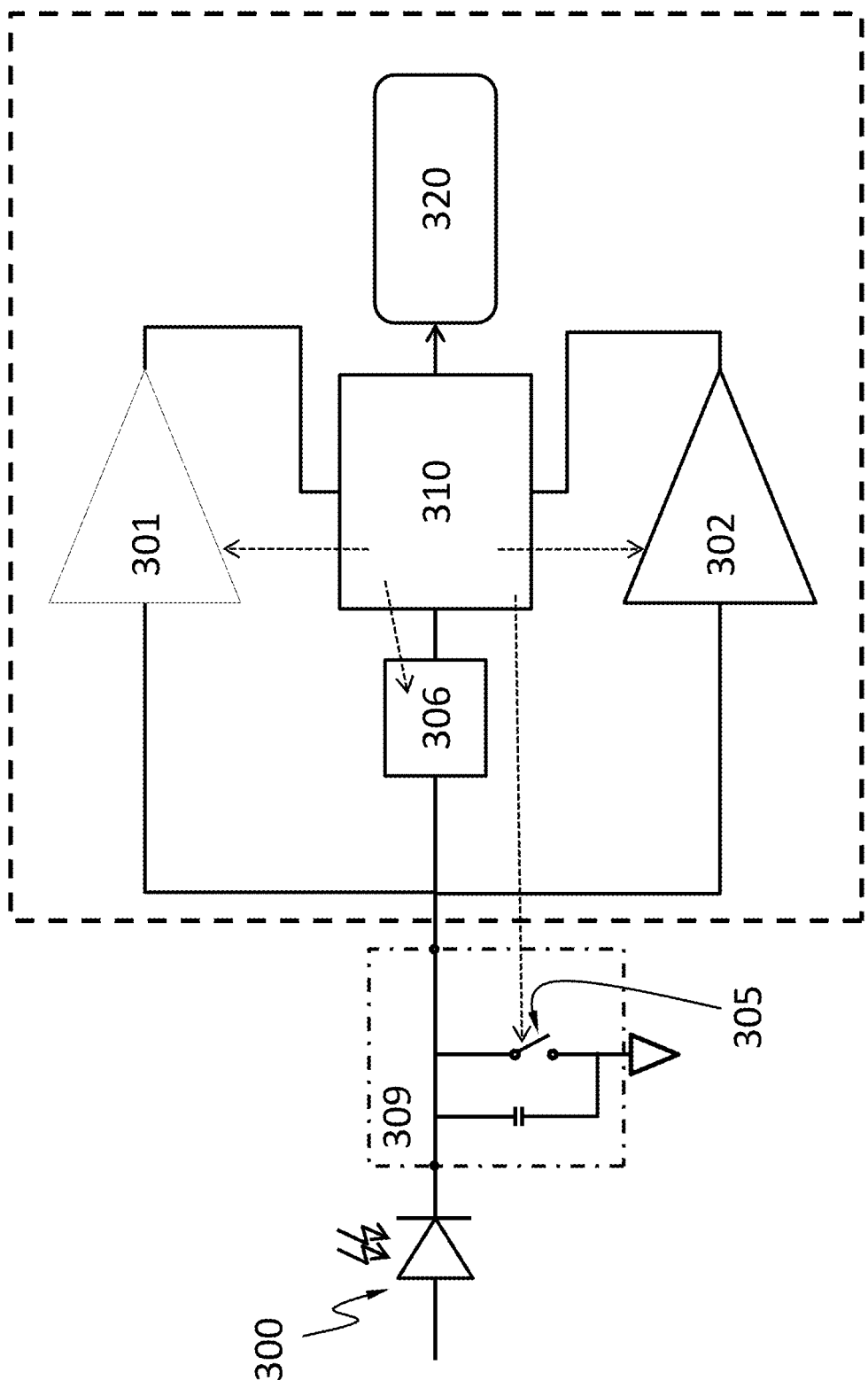

FIG. 17A and FIG. 17B each show a component diagram of the electronic system 121, according to an embodiment. The electronic system 121 may include a first voltage comparator 301, a second voltage comparator 302, a counter 320, a switch 305, a voltmeter 306 and a controller 310.

The first voltage comparator 301 is configured to compare the voltage of an electrode of a diode 300 to a first threshold. The diode may be a diode formed by the first doped region 111, one of the discrete regions 114 of the second doped region 113, and the optional intrinsic region 112. Alternatively, the first voltage comparator 301 is configured to compare the voltage of an electrical contact (e.g., a discrete portion of electrical contact 119B) to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident X-ray photon. The first voltage comparator 301 configured as a continuous comparator is especially suitable when the incident X-ray intensity is relatively high. The first voltage comparator 301 may be a clocked comparator, which has the benefit of lower power consumption. The first voltage comparator 301 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 301 configured as a clocked comparator is especially suitable when the incident X-ray intensity is relatively low. The first threshold may be 5-10%, 10%-20%, 20-30%, 30-40% or 40-50% of the maximum voltage one incident X-ray photon may generate in the diode or the resistor. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, |x|=

$$\begin{cases} x, \text{ if } x \geq 0 \\ -x, \text{ if } x \leq 0 \end{cases}.$$

The second threshold may be 200%-300% of the first threshold. The second threshold may be at least 50% of the maximum voltage one incident X-ray photon may generate in the diode or resistor. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident X-ray. However, having a high speed is often at the cost of power consumption.

The counter 320 is configured to register a number of X-ray photons reaching the diode or resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 310 may connect the electrode to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

Figure 18:
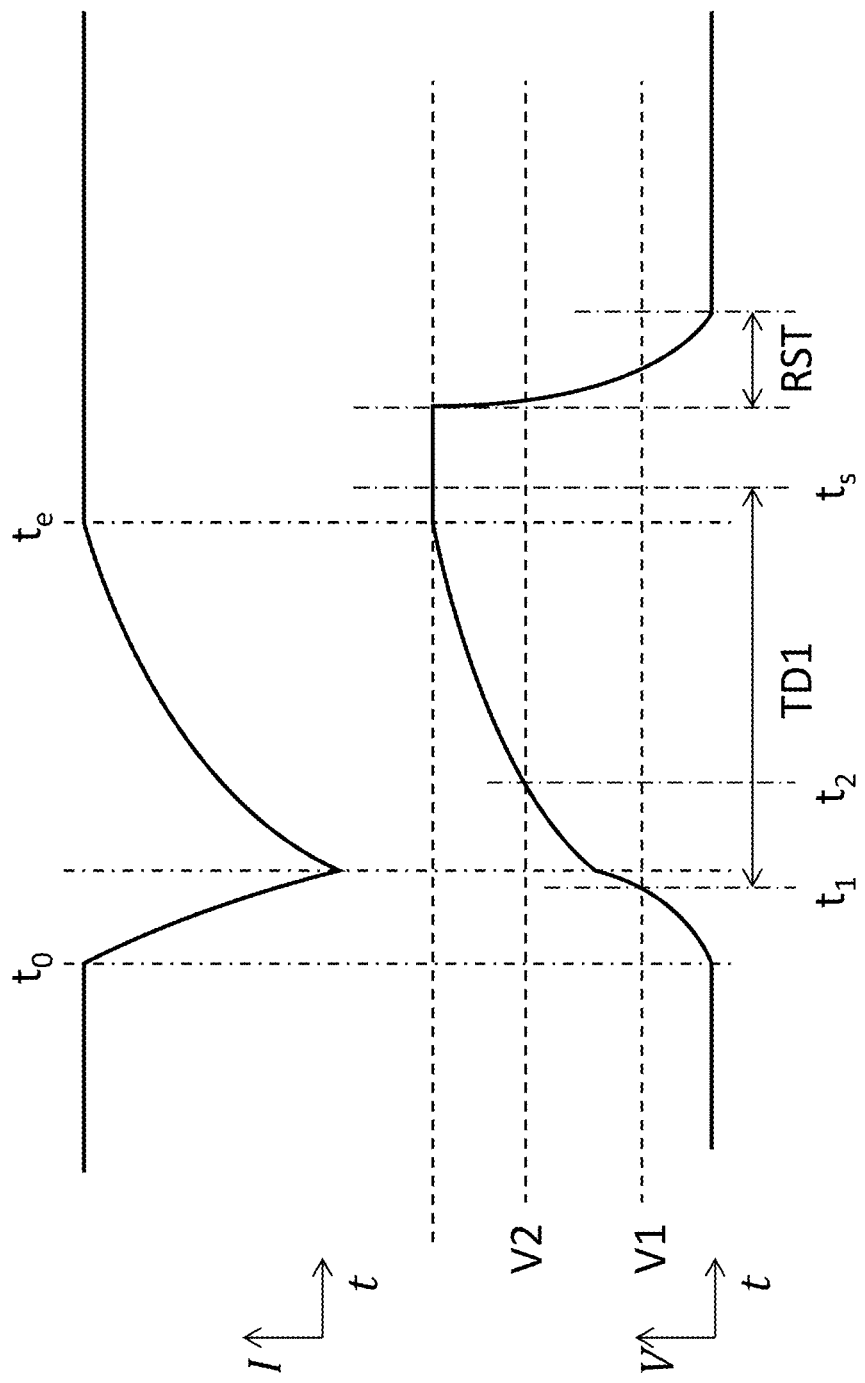
FIG. 18 schematically shows a temporal change of the electric current flowing through an electrode (upper curve) of a diode or an electrical contact of a resistor of an X-ray absorption layer exposed to X-ray, the electric current caused by charge carriers generated by an X-ray photon incident on the X-ray absorption layer, and a corresponding temporal change of the voltage of the electrode (lower curve), according to an embodiment.

The system 121 may include a capacitor module 309 electrically connected to the electrode of the diode 300 or which electrical contact, wherein the capacitor module is configured to collect charge carriers from the electrode. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 18, between $t_0$ to $t_1$, or $t_1$-$t_2$). After the integration period has expired, the capacitor voltage is sampled and then reset by a reset switch. The capacitor module can include a capacitor directly connected to the electrode.

FIG. 18 schematically shows a temporal change of the electric current flowing through the electrode (upper curve) caused by charge carriers generated by an X-ray photon incident on the diode or the resistor, and a corresponding temporal change of the voltage of the electrode (lower curve). The voltage may be an integral of the electric current with respect to time. At time $t_0$, the X-ray photon hits the diode or the resistor, charge carriers start being generated in the diode or the resistor, electric current starts to flow through the electrode of the diode or the resistor, and the absolute value of the voltage of the electrode or electrical contact starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold at time $t_2$, the controller 310 causes the number registered by the counter 320 to increase by one. At time $t_e$, all charge carriers generated by the X-ray photon drift out of the X-ray absorption layer 110. At time $t_s$, the time delay TD1 expires. In the example of FIG. 18, time $t_s$ is after time $t_e$; namely TD1 expires after all charge carriers generated by the X-ray photon drift out of the X-ray absorption layer 110. The rate of change of the voltage is thus substantially zero at $t_s$. The controller 310 may be configured to deactivate the second voltage comparator 302 at expiration of TD1 or at $t_2$, or any time in between.

The controller 310 may be configured to cause the voltmeter 306 to measure the voltage upon expiration of the time delay TD1. In an embodiment, the controller 310 causes the voltmeter 306 to measure the voltage after the rate of change of the voltage becomes substantially zero after the expiration of the time delay TD1. The voltage at this moment is proportional to the amount of charge carriers generated by an X-ray photon, which relates to the energy of the X-ray photon. The controller 310 may be configured to determine the energy of the X-ray photon based on voltage the voltmeter 306 measures. One way to determine the energy is by binning the voltage. The counter 320 may have a sub-counter for each bin. When the controller 310 determines that the energy of the X-ray photon falls in a bin, the controller 310 may cause the number registered in the sub-counter for that bin to increase by one. Therefore, the system 121 may be able to detect an X-ray image and may be able to resolve X-ray photon energies of each X-ray photon.

After TD1 expires, the controller 310 connects the electrode to an electric ground for a reset period RST to allow charge carriers accumulated on the electrode to flow to the ground and reset the voltage. After RST, the system 121 is ready to detect another incident X-ray photon. Implicitly, the rate of incident X-ray photons the system 121 can handle in the example of FIG. 18 is limited by 1/(TD1+RST). If the first voltage comparator 301 has been deactivated, the controller 310 can activate it at any time before RST expires. If the controller 310 has been deactivated, it may be activated before RST expires.

Figure 19:
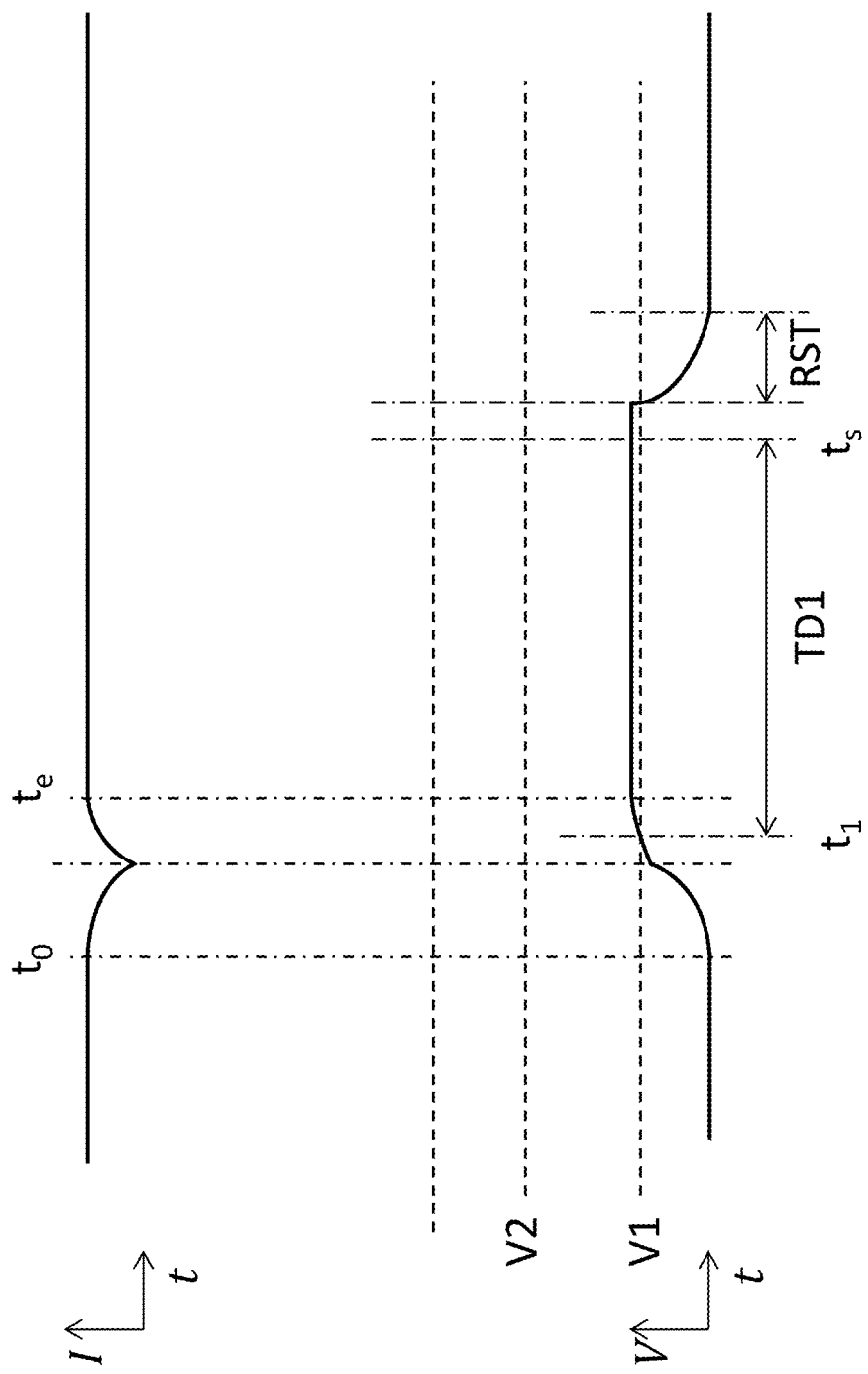
FIG. 19 schematically shows a temporal change of the electric current flowing through the electrode (upper curve) caused by noise (e.g., dark current), and a corresponding temporal change of the voltage of the electrode (lower curve), in the electronic system operating in the way shown in FIG. 18, according to an embodiment.

FIG. 19 schematically shows a temporal change of the electric current flowing through the electrode (upper curve) caused by noise (e.g., dark current, background radiation, scattered X-rays, fluorescent X-rays, shared charges from adjacent pixels), and a corresponding temporal change of the voltage of the electrode (lower curve), in the system 121 operating in the way shown in FIG. 18. At time $t_0$, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD1 and the controller 310 may deactivate the first voltage comparator 301 at the beginning of TD1. During TD1 (e.g., at expiration of TD1), the controller 310 activates the second voltage comparator 302. The noise is very unlikely large enough to cause the absolute value of the voltage to exceed the absolute value of V2 during TD1. Therefore, the controller 310 does not cause the number registered by the counter 320 to increase. At time $t_e$, the noise ends. At time $t_s$, the time delay TD1 expires. The controller 310 may be configured to deactivate the second voltage comparator 302 at expiration of TD1. The controller 310 may be configured not to cause the voltmeter 306 to measure the voltage if the absolute value of the voltage does not exceed the absolute value of V2 during TD1. After TD1 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 20:
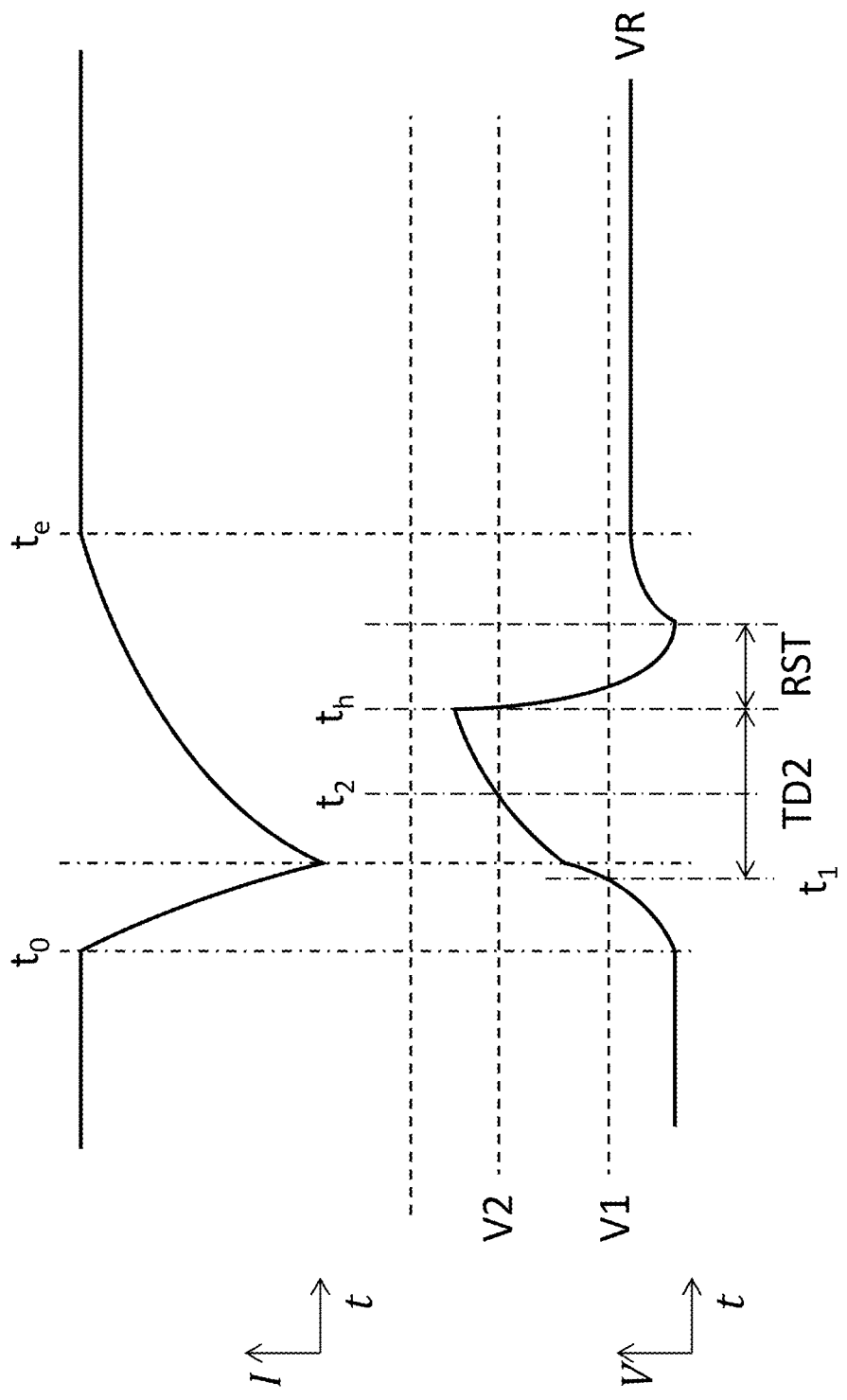
FIG. 20 schematically shows a temporal change of the electric current flowing through an electrode (upper curve) of the X-ray absorption layer exposed to X-ray, the electric current caused by charge carriers generated by an X-ray photon incident on the X-ray absorption layer, and a corresponding temporal change of the voltage of the electrode (lower curve), when the electronic system operates to detect incident X-ray photons at a higher rate, according to an embodiment.

FIG. 20 schematically shows a temporal change of the electric current flowing through the electrode (upper curve) caused by charge carriers generated by an X-ray photon incident on the diode or the resistor, and a corresponding temporal change of the voltage of the electrode (lower curve), when the system 121 operates to detect incident X-ray photons at a rate higher than 1/(TD1+RST). The voltage may be an integral of the electric current with respect to time. At time $t_0$, the X-ray photon hits the diode or the resistor, charge carriers start being generated in the diode or the resistor, electric current starts to flow through the electrode of the diode or the electrical contact of resistor, and the absolute value of the voltage of the electrode or the electrical contact starts to increase. At time $t_1$, the first voltage comparator 301 determines that the absolute value of the voltage equals or exceeds the absolute value of the first threshold V1, and the controller 310 starts a time delay TD2 shorter than TD1, and the controller 310 may deactivate the first voltage comparator 301 at the beginning of TD2. If the controller 310 is deactivated before $t_1$, the controller 310 is activated at $t_1$. During TD2 (e.g., at expiration of TD2), the controller 310 activates the second voltage comparator 302. If during TD2, the second voltage comparator 302 determines that the absolute value of the voltage equals or exceeds the absolute value of the second threshold at time $t_2$, the controller 310 causes the number registered by the counter 320 to increase by one. At time $t_e$, all charge carriers generated by the X-ray photon drift out of the X-ray absorption layer 110. At time $t_h$, the time delay TD2 expires. In the example of FIG. 20, time $t_h$ is before time $t_e$; namely TD2 expires before all charge carriers generated by the X-ray photon drift out of the X-ray absorption layer 110. The rate of change of the voltage is thus substantially non-zero at $t_h$. The controller 310 may be configured to deactivate the second voltage comparator 302 at expiration of TD2 or at $t_2$, or any time in between.

The controller 310 may be configured to extrapolate the voltage at $t_e$ from the voltage as a function of time during TD2 and use the extrapolated voltage to determine the energy of the X-ray photon.

After TD2 expires, the controller 310 connects the electrode to an electric ground for a reset period RST to allow charge carriers accumulated on the electrode to flow to the ground and reset the voltage. In an embodiment, RST expires before $t_e$. The rate of change of the voltage after RST may be substantially non-zero because all charge carriers generated by the X-ray photon have not drifted out of the X-ray absorption layer 110 upon expiration of RST before $t_e$. The rate of change of the voltage becomes substantially zero after $t_e$ and the voltage stabilized to a residue voltage VR after $t_e$. In an embodiment, RST expires at or after $t_e$, and the rate of change of the voltage after RST may be substantially zero because all charge carriers generated by the X-ray photon drift out of the X-ray absorption layer 110 at $t_e$. After RST, the system 121 is ready to detect another incident X-ray photon. If the first voltage comparator 301 has been deactivated, the controller 310 can activate it at any time before RST expires. If the controller 310 has been deactivated, it may be activated before RST expires.

Figure 21:
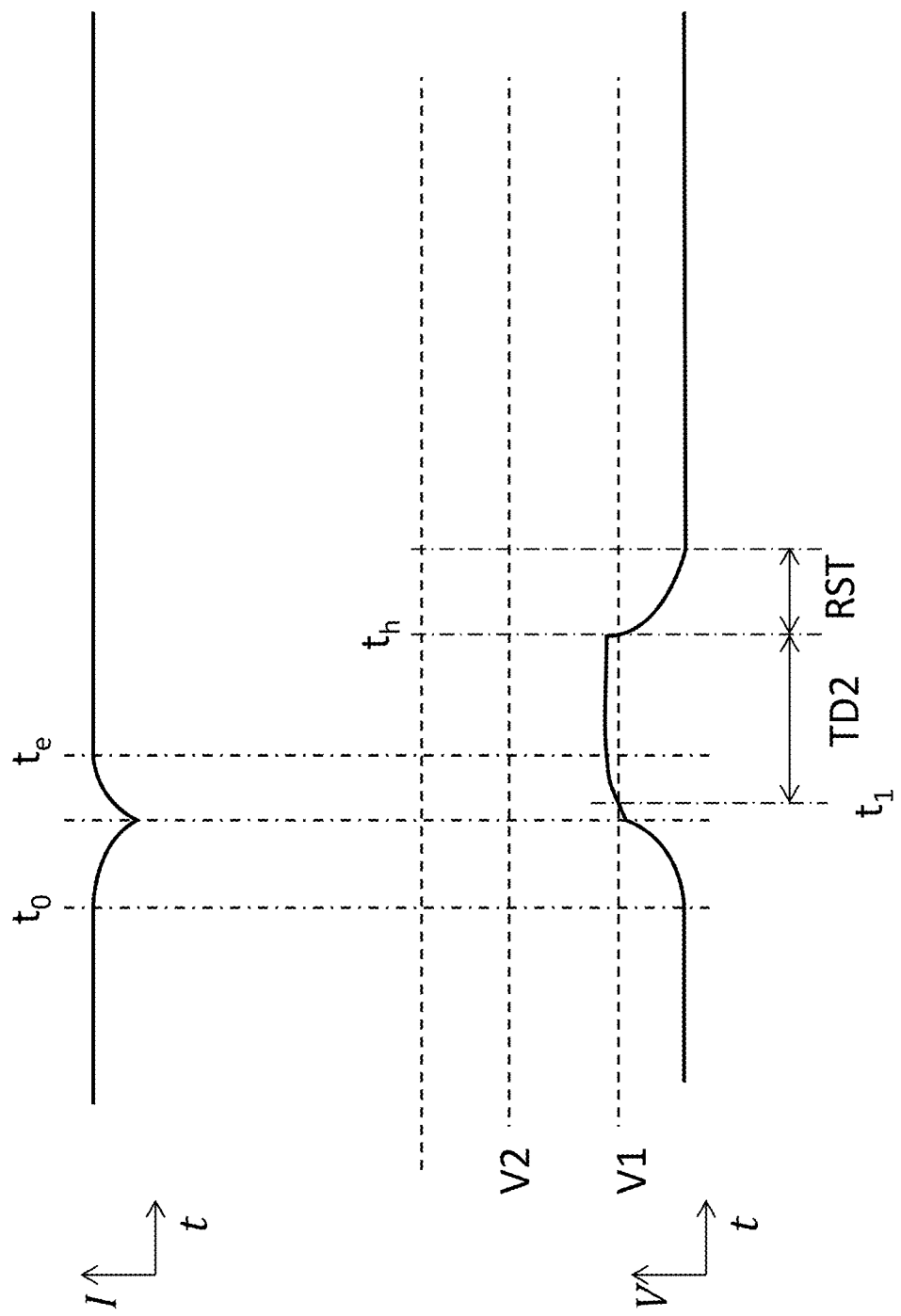
FIG. 21 schematically shows a temporal change of the electric current flowing through the electrode (upper curve) caused by noise (e.g., dark current), and a corresponding temporal change of the voltage of the electrode (lower curve), in the electronic system operating in the way shown in FIG. 20, according to an embodiment.

FIG. 21 schematically shows a temporal change of the electric current flowing through the electrode (upper curve) caused by noise (e.g., dark current, background radiation, scattered X-rays, fluorescent X-rays, shared charges from adjacent pixels), and a corresponding temporal change of the voltage of the electrode (lower curve), in the system 121 operating in the way shown in FIG. 20. At time $t_0$, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD2 and the controller 310 may deactivate the first voltage comparator 301 at the beginning of TD2. During TD2 (e.g., at expiration of TD2), the controller 310 activates the second voltage comparator 302. The noise is very unlikely large enough to cause the absolute value of the voltage to exceed the absolute value of V2 during TD2. Therefore, the controller 310 does not cause the number registered by the counter 320 to increase. At time $t_e$, the noise ends. At time $t_h$, the time delay TD2 expires. The controller 310 may be configured to deactivate the second voltage comparator 302 at expiration of TD2. After TD2 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 22:
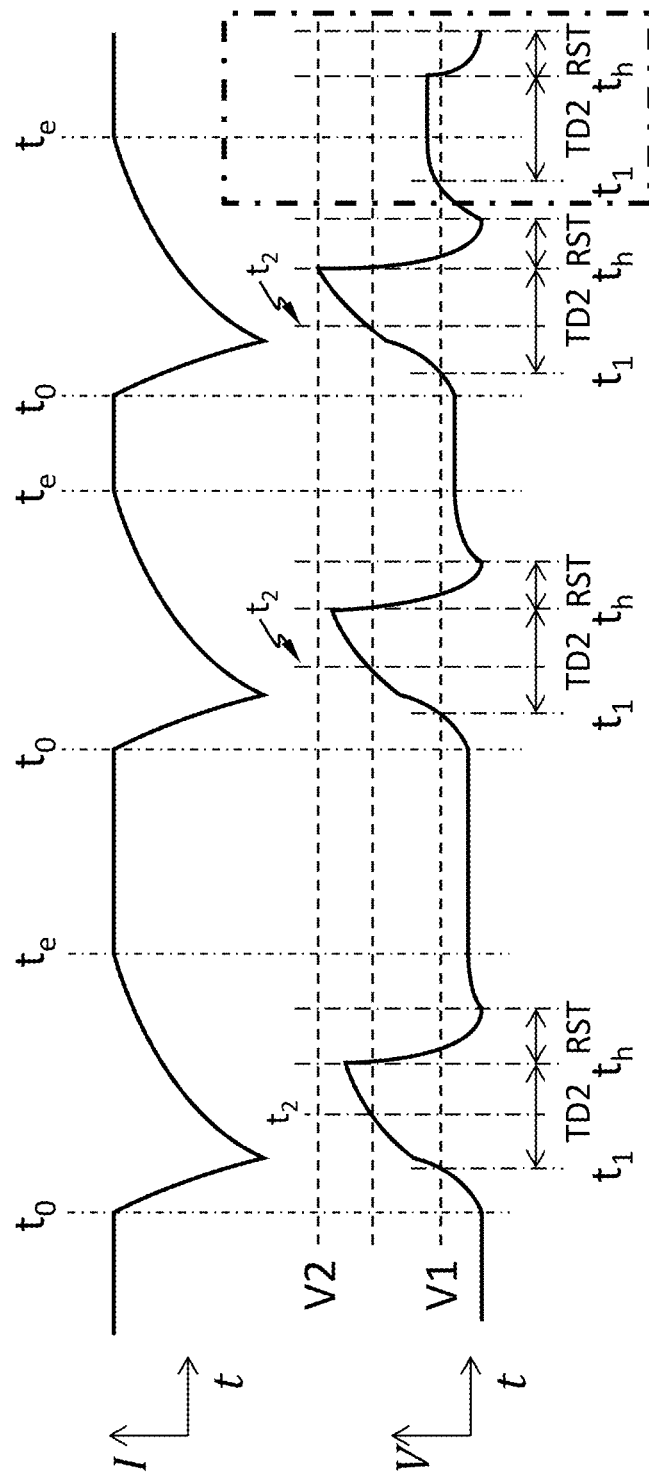
FIG. 22 schematically shows a temporal change of the electric current flowing through the electrode (upper curve) caused by charge carriers generated by a series of X-ray photons incident on the X-ray absorption layer, and a corresponding temporal change of the voltage of the electrode, in the electronic system operating in the way shown in FIG. 20 with RST expires before $t_e$, according to an embodiment.

FIG. 22 schematically shows a temporal change of the electric current flowing through the electrode (upper curve) caused by charge carriers generated by a series of X-ray photons incident on the diode or the resistor, and a corresponding temporal change of the voltage of the electrode (lower curve), in the system 121 operating in the way shown in FIG. 20 with RST expires before $t_e$. The voltage curve caused by charge carriers generated by each incident X-ray photon is offset by the residue voltage before that photon. The absolute value of the residue voltage successively increases with each incident photon. When the absolute value of the residue voltage exceeds V1 (see the dotted rectangle in FIG. 22), the controller starts the time delay TD2 and the controller 310 may deactivate the first voltage comparator 301 at the beginning of TD2. If no other X-ray photon incidence on the diode or the resistor during TD2, the controller connects the electrode to the electrical ground during the reset time period RST at the end of TD2, thereby resetting the residue voltage. The residue voltage thus does not cause an increase of the number registered by the counter 320.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An image sensor comprising:
a plurality of X-ray detectors;
an actuator configured to move the plurality of X-ray detectors to a plurality of positions, wherein the image sensor is configured to capture, by using the detectors, images of portions of a scene at the positions, respectively, and configured to form an image of the scene by stitching the images of the portions;
wherein at least one of the plurality of X-ray detectors comprises an X-ray absorption layer and an electronics layer;
wherein the X-ray absorption layer comprises an electrode;
wherein the electronics layer comprises an electronics system;
wherein the electronics system comprises:
a first voltage comparator configured to compare a voltage of the electrode to a first threshold,
a second voltage comparator configured to compare the voltage to a second threshold,
a counter configured to register a number of X-ray photons reaching the X-ray absorption layer, and
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the number registered by the counter to increase by one, if the second voltage comparator determines that an absolute value of the voltage equals or exceeds an absolute value of the second threshold.

2. The image sensor of claim 1, wherein the plurality of X-ray detectors are spaced apart.

3. The image sensor of claim 1, comprising a collimator with a plurality of X-ray transmitting zones and an X-ray blocking zone;
wherein the X-ray blocking zone is configured to block X-ray that would otherwise incident on a dead zone of the image sensor, and the X-ray transmitting zones are configured to allow at least a portion of X-ray that would incident on active areas of the image sensor.

4. The image sensor of claim 3, wherein the actuator is configured to move the collimator such that an alignment of the X-ray detectors with the X-ray transmitting zones and the X-ray blocking zone is maintained at the positions.

5. The image sensor of claim 1, wherein at least some of the plurality of X-ray detectors are arranged in staggered rows and on a plane perpendicular to a direction of some radiations used in the capture of the images of the portions.

6. The image sensor of claim 5, wherein X-ray detectors in a same row are uniform in size; wherein a distance between two neighboring X-ray detectors in a same row is greater than a width of one X-ray detector in the same row in an extending direction of the row and is less than twice that width.

7. The image sensor of claim 1, wherein active areas of the X-ray detectors tessellate the scene at the positions.

8. The image sensor of claim 1, wherein the actuator comprises a robotic arm.

9. The image sensor of claim 1, wherein at least some of the plurality of X-ray detectors comprise multiple layers of detectors.

10. The image sensor of claim 1, wherein at least some of the plurality of X-ray detectors are rectangular in shape.

11. The image sensor of claim 1, wherein at least some of the plurality of X-ray detectors are hexagonal in shape.

12. The image sensor of claim 1, wherein the actuator comprises a control unit configured to determine the positions.

13. The image sensor of claim 1, wherein the electronics system further comprises a capacitor module electrically connected to the electrode, wherein the capacitor module is configured to collect charge carriers from the electrode.

14. The image sensor of claim 1, wherein the controller is configured to activate the second voltage comparator at a beginning or expiration of the time delay.

15. The image sensor of claim 1, wherein the electronics system further comprises a voltmeter, wherein the controller is configured to cause the voltmeter to measure the voltage upon expiration of the time delay.

16. The image sensor of claim 1, wherein the controller is configured to determine an X-ray photon energy based on a value of the voltage measured upon expiration of the time delay.

17. The image sensor of claim 1, wherein the controller is configured to connect the electrode to an electrical ground.

18. The image sensor of claim 1, wherein a rate of change of the voltage is substantially zero at expiration of the time delay.

19. The image sensor of claim 1, wherein a rate of change of the voltage is substantially non-zero at expiration of the time delay.

20. A system comprising the image sensor of claim 1 and an X-ray source, wherein the system is configured to perform X-ray radiography on human chest or abdomen.

21. A system comprising the image sensor of claim 1 and an X-ray source, wherein the system is configured to perform X-ray radiography on human mouth.

22. A cargo scanning or non-intrusive inspection (NII) system, comprising the image sensor of claim 1 and an X-ray source, wherein the cargo scanning or non-intrusive inspection (NII) system is configured to form an image using backscattered X-ray.

23. A cargo scanning or non-intrusive inspection (NII) system, comprising the image sensor of claim 1 and an X-ray source, wherein the cargo scanning or non-intrusive inspection (NII) system is configured to form an image using X-ray transmitted through an object inspected.

24. A full-body scanner system comprising the image sensor of claim 1 and an X-ray source.

25. An X-ray computed tomography (X-ray CT) system comprising the image sensor of claim 1 and an X-ray source.

26. An electron microscope comprising the image sensor of claim 1, an electron source and an electronic optical system.

27. A system comprising the image sensor of claim 1, wherein the system is an X-ray telescope, or an X-ray microscopy, or wherein the system is configured to perform mammography, industrial defect detection, microradiography, casting inspection, weld inspection, or digital subtraction angiography.

28. A method of forming an image of a scene using the image sensor of claim 1, the method comprising:
   taking a first image of a first portion of the scene by positioning the X-ray detectors to a first position;
   taking a second image of a second portion of the scene by positioning the X-ray detectors to a second position;
   forming the image of the scene by stitching at least the first image and the second image.

29. The method of claim 28, wherein the first and the second images have a spatial overlap.

30. The method of claim 28, wherein the image sensor further comprises a collimator; wherein the method further comprises positioning the collimator before taking the first and the second images.

* * * * *